(12) United States Patent
Machyna et al.

(10) Patent No.: US 11,530,435 B2
(45) Date of Patent: Dec. 20, 2022

(54) COMPOSITIONS AND METHODS FOR IMPROVED RNA CAPTURE

(71) Applicant: YALE UNIVERSITY, New Haven, CT (US)

(72) Inventors: Martin Machyna, New Haven, CT (US); Matthew Simon, New Haven, CT (US)

(73) Assignee: Yale University, New Haven, CT (US)

( * ) Notice: Subject to any disclaimer, the term of this patent is extended or adjusted under 35 U.S.C. 154(b) by 442 days.

(21) Appl. No.: 16/412,527

(22) Filed: May 15, 2019

(65) Prior Publication Data

US 2019/0352696 A1 Nov. 21, 2019

Related U.S. Application Data

(60) Provisional application No. 62/671,538, filed on May 15, 2018.

(51) Int. Cl.
*C12Q 1/6804* (2018.01)
*C12Q 1/6816* (2018.01)

(52) U.S. Cl.
CPC ......... *C12Q 1/6804* (2013.01); *C12Q 1/6816* (2013.01)

(58) Field of Classification Search
CPC ... C12Q 1/68; C12Q 2537/1373; C07H 21/00
See application file for complete search history.

(56) References Cited

U.S. PATENT DOCUMENTS

| | | | | |
|---|---|---|---|---|
| 2010/0021901 A1* | 1/2010 | Yin | ...................... | C12Q 1/6818 435/6.12 |
| 2013/0123123 A1* | 5/2013 | Chang | .................. | C12Q 1/6841 506/9 |
| 2015/0004598 A1* | 1/2015 | Gao | ...................... | C12Q 1/6841 435/6.11 |
| 2018/0030504 A1* | 2/2018 | Nolan | ................. | G01N 33/5308 |
| 2019/0352696 A1* | 11/2019 | Machyna | .............. | C12Q 1/6816 |
| 2021/0403983 A1* | 12/2021 | Chen | ...................... | C12Q 1/682 |

OTHER PUBLICATIONS

Batz et al.The mRNA-Bound Proteome and Its Global Occupancy Profile on Protein-Coding Transcripts. Molecular Cell 46 : 674-690 (Year: 2012).*
Licatalosi et al.,HITS-CLIP yields genome-wide insights into brain alternative RNA processing. Nature 456: 464 (Year: 2008).*
Milek et al., Seminars in Cell & Developmental Biology 23 : 206-212 (Year: 2012).*
Wheeler et al., Advances and challenges in the detection of transcriptome-wide protein-RNA interactions. WIREs RNA 9 : e1436 (Jan./Feb. 2018) (Year: 2018).*
Braasch and Corey, 2001, "Locked nucleic acid (LNA): fine-tuning the recognition of DNA and RNA," Chem. Biol, 8:1-7.
Castello et al., 2013, "System-wide identification of RNA-binding proteins by interactome capture," Nature protocols 8(3): 491-500.
Chaligne et al., 2015, "The inactive X chromosome is epigenetically unstable and transcriptionally labile in breast cancer," Genome research, 25(4): 488-503.
Chaligne et al., 2014, "X-chromosome inactivation in development and cancer," FEBS Lett, 588(15): 2514-2522.
Demidov and Frank-Kamenetskii, 2004, "Two sides of the coin: affinity and specificity of nucleic acid interactions," Trends in biochemical sciences 29(2): 62-71.
Diaz-Perez et al., 2006, "A Deletion at the Mouse Xist Gene Exposes Trans-effects That Alter the Heterochromatin of the Inactive X Chromosome and the Replication Time and DNA Stability of Both X Chromosomes," Genetics, 174:1115-1133.
Donley et al., 2013, "Asynchronous Replication, Mono-Allelic Expression, and Long Range Cis-Effects of ASAR6," PLoS Genet, 9:e1003423.
Donley et al., 2015, "ASAR15, A cis-Acting Locus that Controls Chromosome-Wide Replication Timing and Stability of Human Chromosome 15," PLoS Genet, 11:e1004923.
Dunford et al., 2017, "Tumor-suppressor genes that escape from X-inactivation contribute to cancer sex bias," Nature genetics 49(1): 10-16.
Engreitz et al., 2013, "The Xist lncRNA exploits three-dimensional genome architecture to spread across the X chromosome," Science 341(6147): 1237973.
Finnegan, 2012, "Retrotransposons," Curr Biol 22, R432-437.
Hall et al., 2014, "Stable C0T-1 repeat RNA is abundant and is associated with euchromatic interphase chromosomes," Cell, 156:907-919.
Machyna and Simon, "Catching RNAs on chromatin using hybridization capture methods," Briefings in Functional Genomics, 17(2), 2018, 96-103.
Mondal et al., 2010, "Characterization of the RNA content of chromatin," Genome Res. 20:899-907.
Padeken et al., 2015, "Repeat DNA in genome organization and stability," Curr. Opin. Genet. Dev. 31:12-19.
Palazzo and Gregory, 2014, "The Case for Junk DNA," PLoS Genet, 10:e1004351.
Quinn et al., 2014, "Revealing long noncoding RNA architecture and functions using domain-specific chromatin isolation by RNA purification," Nature biotechnology 32(9): 933-940.
Rogell et al., 2017, "Specific RNP capture with antisense LNA/DNA mixmers," RNA, 23(8): 1290-1302.
Simon et al., 2011, "The genomic binding sites of a noncoding RNA," Proc Natl Acad Sci U S A 108(51): 20497-20502.
Simon et al., 2013, "High-resolution Xist binding maps reveal two-step spreading during X-chromosome inactivation," Nature, 504:465-469.
Simon, 2016, "Insight into lncRNA biology using hybridization capture analyses," Biochim Biophys Acta, 1859(1): 121-127.

(Continued)

*Primary Examiner* — Ethan C Whisenant
(74) *Attorney, Agent, or Firm* — Riverside Law LLP

(57) ABSTRACT

Disclosed herein are compositions and methods for detecting RNA binding sites and RNA interacting partners involving the use of a modified capture oligonucleotide having a dual toehold design.

10 Claims, 21 Drawing Sheets

Specification includes a Sequence Listing.

(56) References Cited

OTHER PUBLICATIONS

Thayer, 2012, "Mammalian chromosomes contain cis-acting elements that control replication timing, mitotic condensation and stability of entire chromosomes," Bioessays, 34:760-770.
Wahlestedt et al., 2000, "Potent and nontoxic antisense oligonucleotides containing locked nucleic acids," Proc Natl Acad Sci USA, 97:5633-5638.
Wang and Zhang, 2015, "Simulation-guided DNA probe design for consistently ultraspecific hybridization," Nat Chem 7, 545-553.
West et al., 2014, "The long noncoding RNAs NEAT1 and MALAT1 bind active chromatin sites," Mol Cell, 55:791-802.
Wu et al., 2015, "Continuously tunable nucleic acid hybridization probes," Nat Methods, 12(12):1191-1196.
You et al., 2006, "Design of LNA probes that improve mismatch discrimination," Nucleic Acids Res, 34:e60.
Zhang et al., 2012, "Optimizing the specificity of nucleic acid hybridization," Nat Chem, 4:208-214.

\* cited by examiner $\Delta G_{rxn} = \Delta G_{TH1} + (\Delta G_{T:CO} - \Delta G_{CO:PO}) - \Delta G_{TH2}$ 1) RNA PO
2) LNA only in Central region of CO $\Delta G_{T:CO} = \Delta G_{CO:PO}$ $\Delta G_{rxn} = \Delta G_{TH1} - \Delta G_{TH2}$

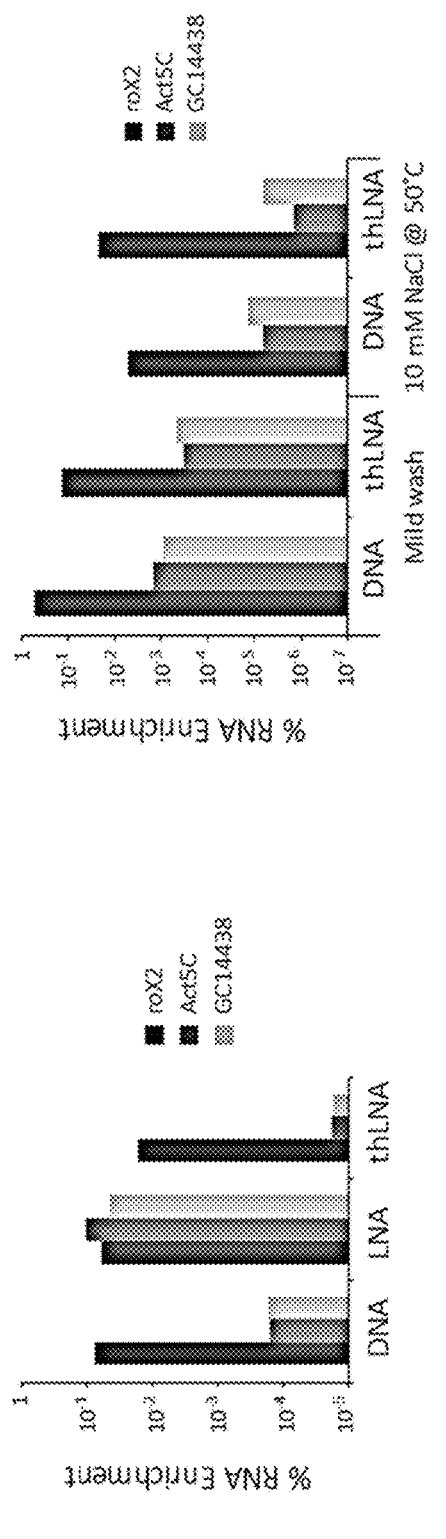
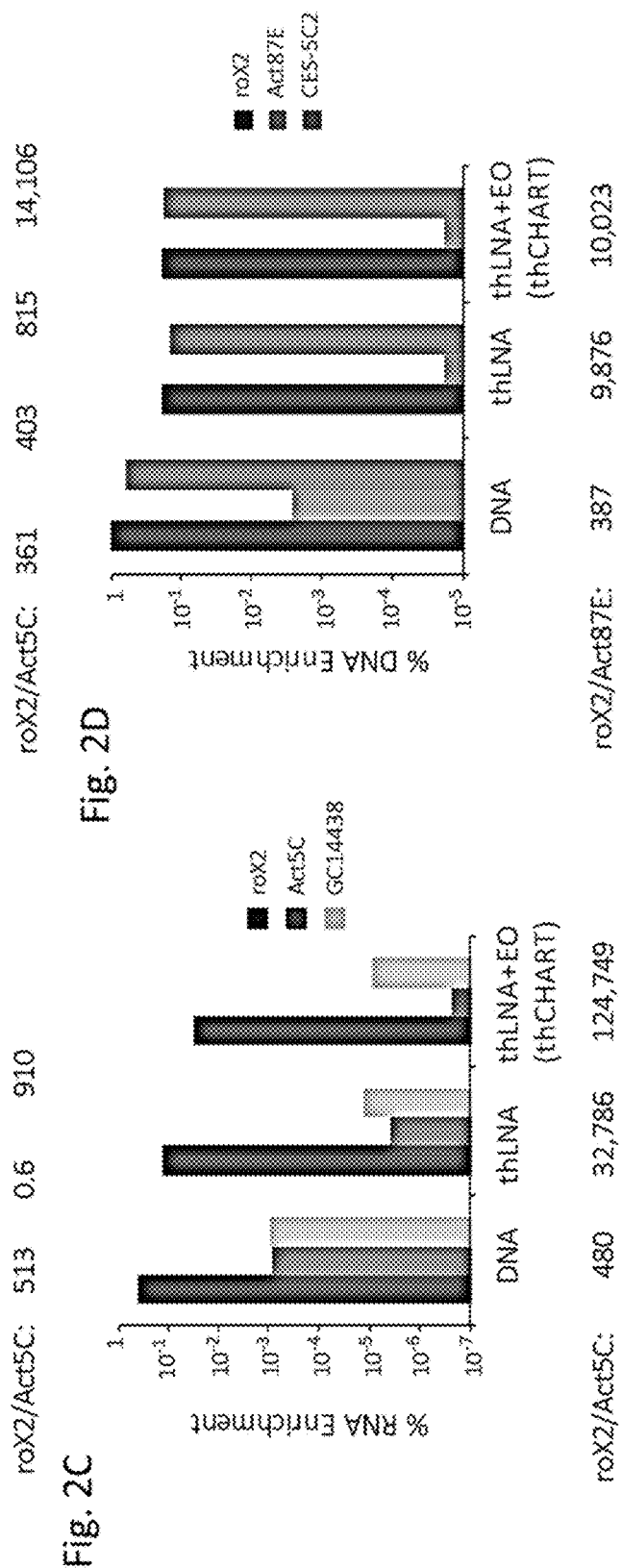
Fig. 2A, Fig. 2B, Fig. 2C, Fig. 2D

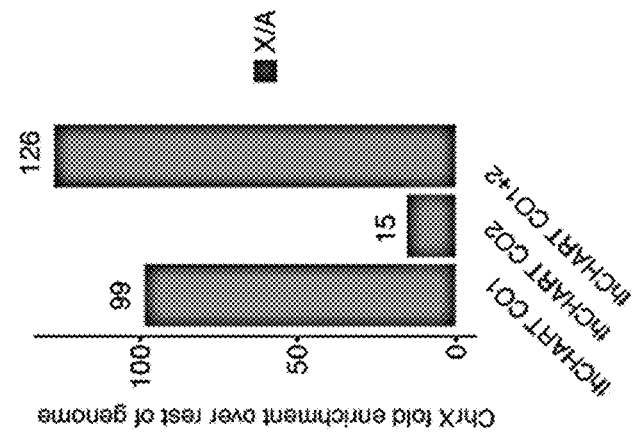
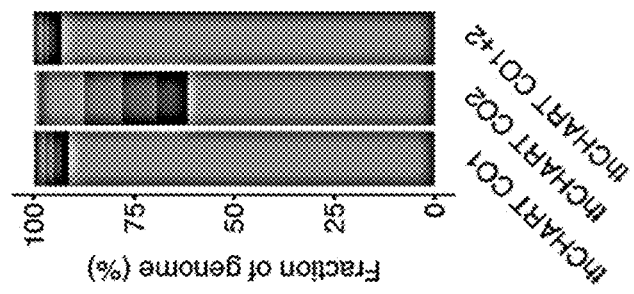
Fig. 5A
Fig. 5B
Fig. 5C

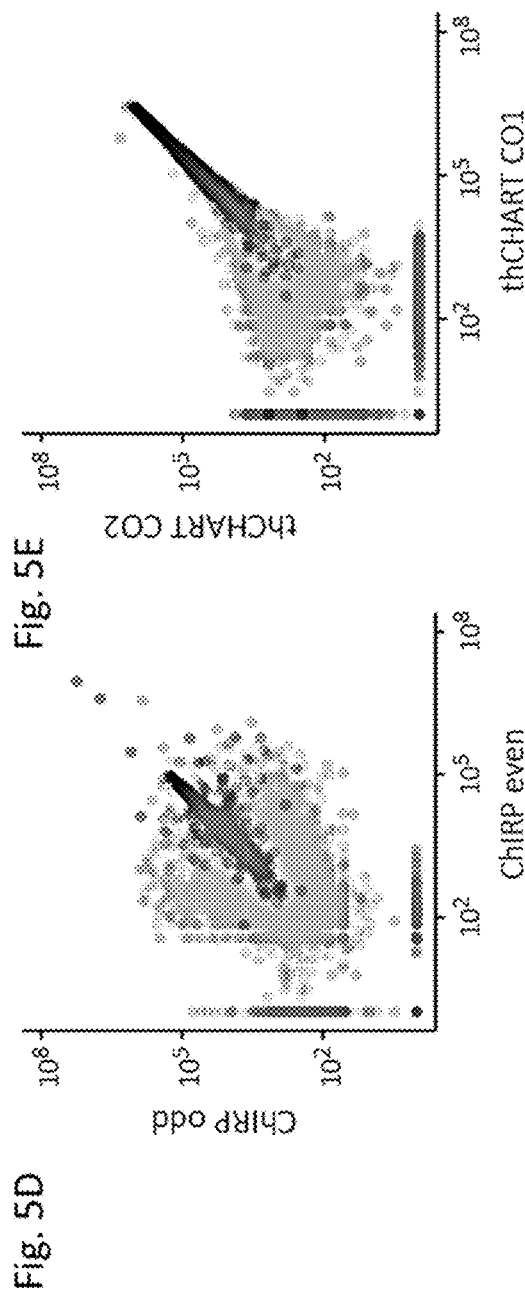
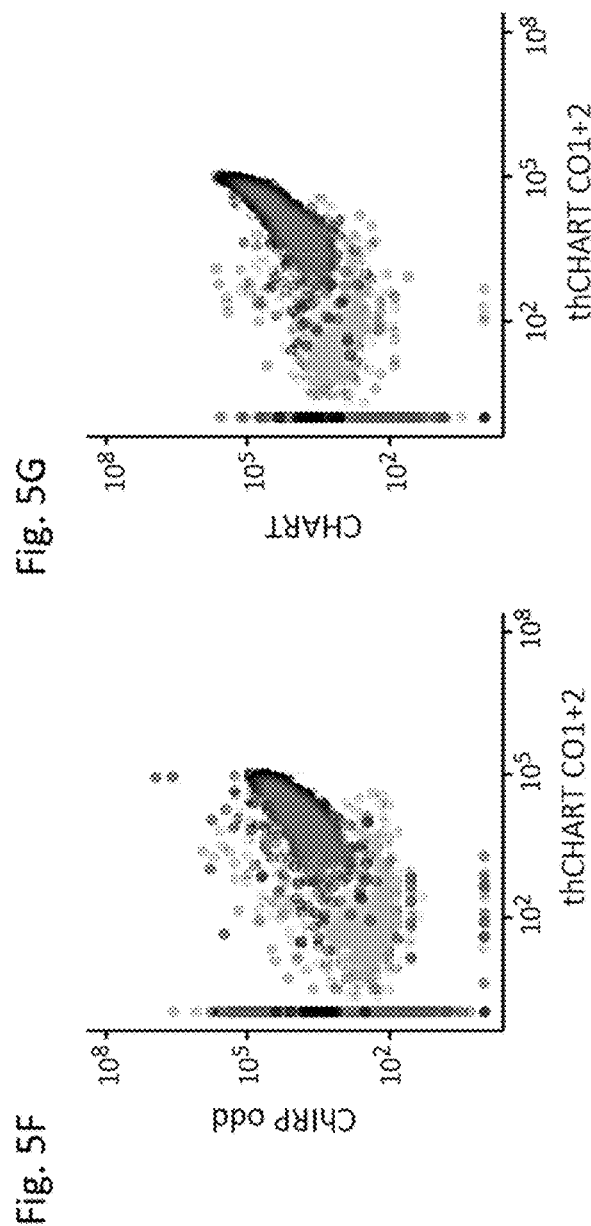

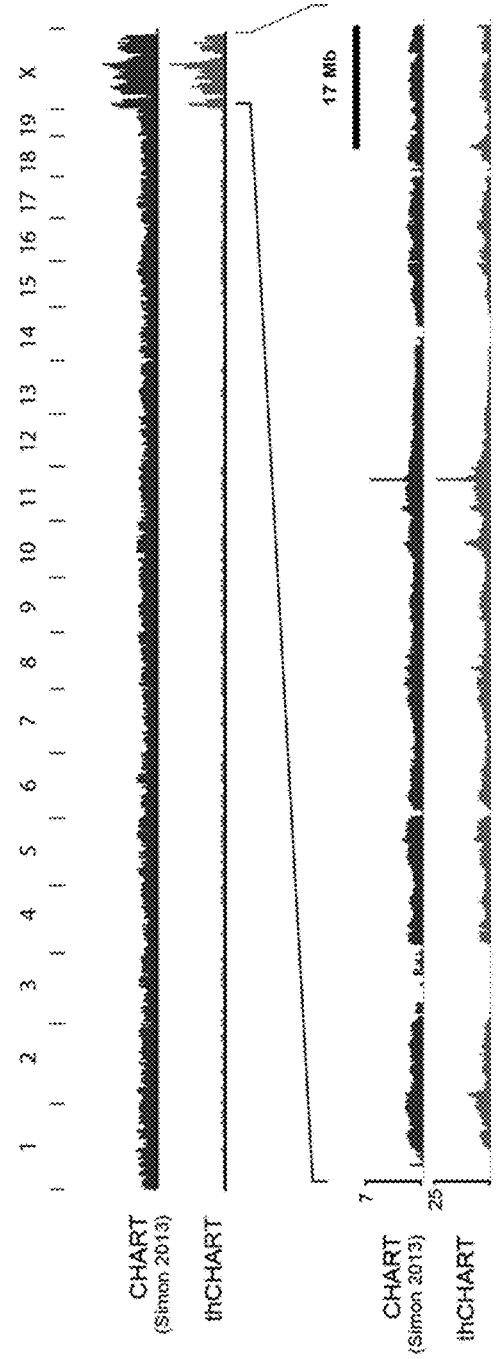
Fig. 6A
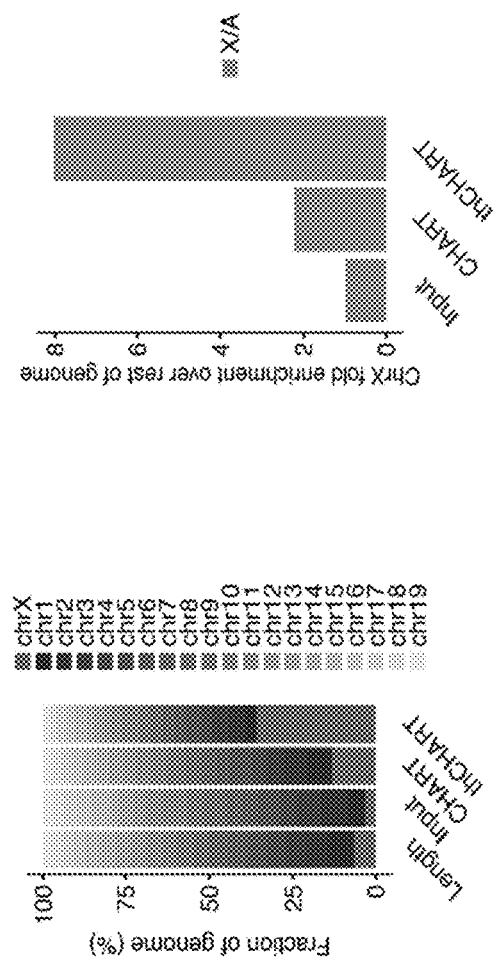
Fig. 6B
Fig. 6C

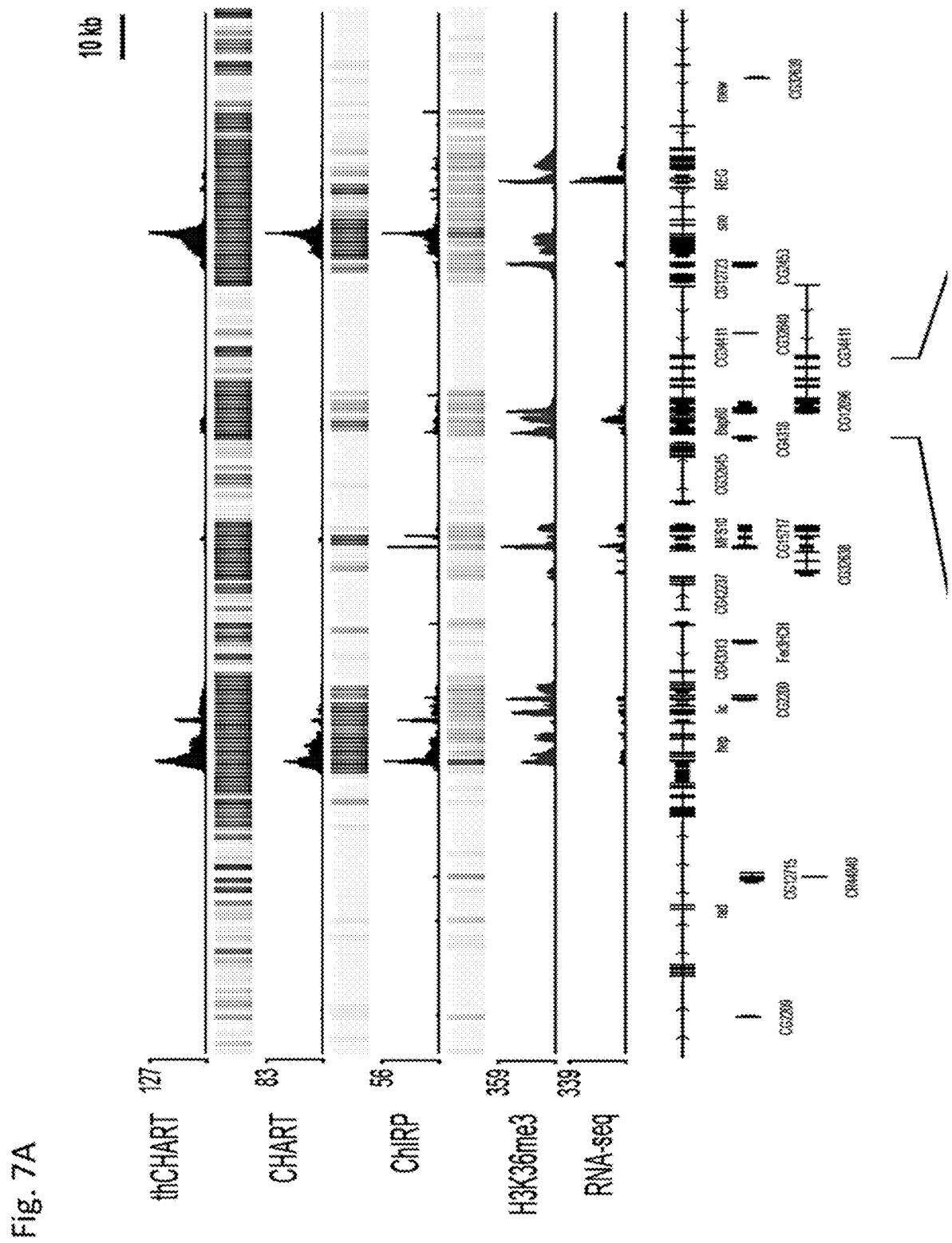

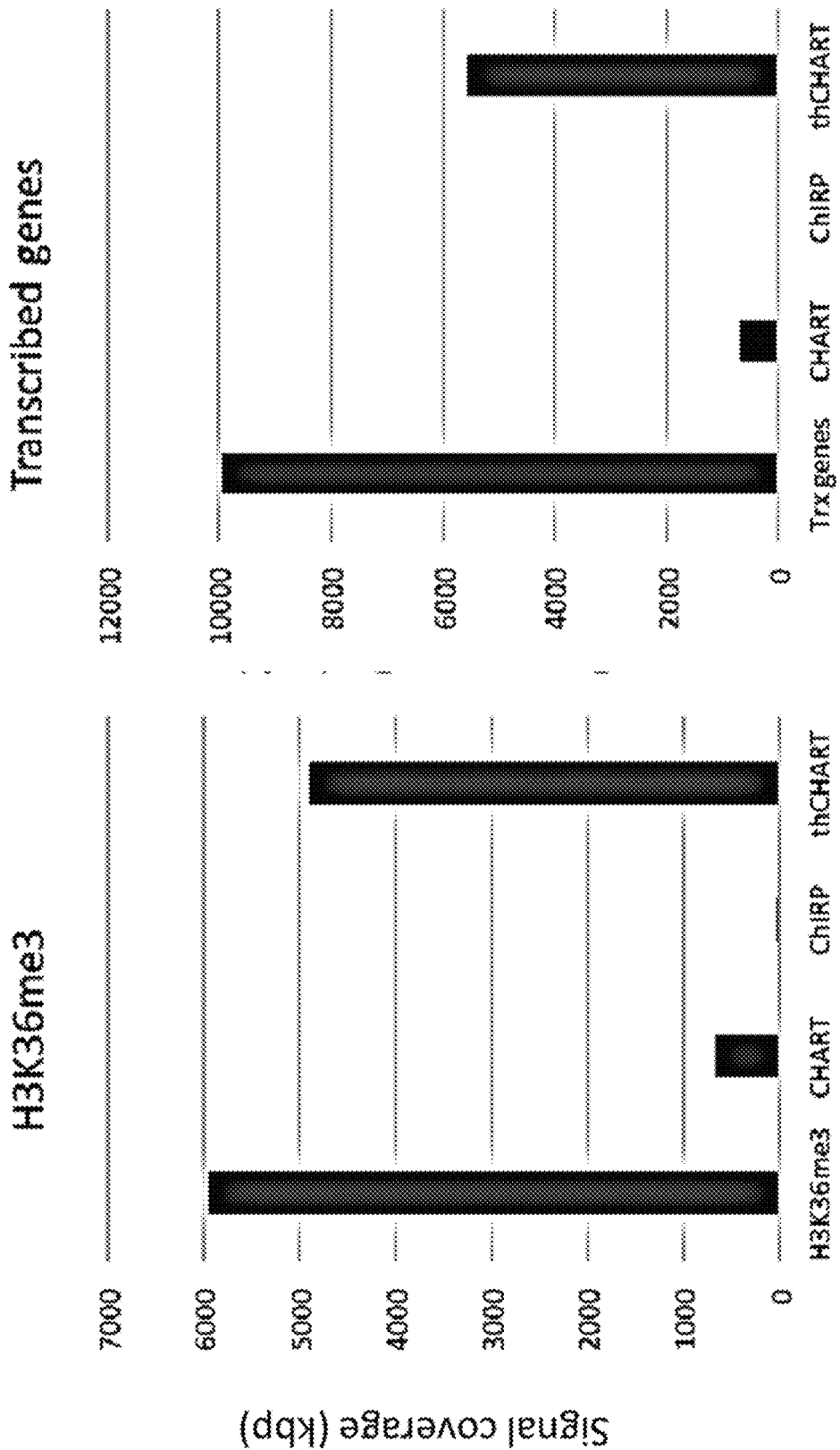

SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Chemically synthesized

<400> SEQUENCE: 1
tatgtaacac caatttaccc tttcggacta tagt         34

<210> SEQ ID NO 2
<211> LENGTH: 24
<212> TYPE: RNA
<213> ORGANISM: Artificial Sequence
<220> FEATURE:
<223> OTHER INFORMATION: Chemically synthesized

<400> SEQUENCE: 2
acuauagucc gaaaggguaa auug         24

COMPOSITIONS AND METHODS FOR IMPROVED RNA CAPTURE

CROSS REFERENCE TO RELATED APPLICATIONS

This application claims priority to U.S. Provisional Application No. 62/671,538, filed May 15, 2018 which is hereby incorporated by reference herein in its entirety.

STATEMENT OF GOVERNMENT SUPPORT

This invention was made with government support under Grant No. 1DP2HD083992 awarded by the National Institutes of Health. The government has certain rights in the invention.

BACKGROUND

Recent genomic research has revealed that mammalian genomes are more prevalently transcribed than previously thought. Mammalian genomes express not only protein-coding mRNAs but also a large repertoire of non-coding RNAs (ncRNAs) that have regulatory functions in different layers of cell physiology. Many ncRNAs appear to act directly on chromatin, as exemplified by various characterized long non-coding RNAs (lncRNAs) and play role in regulating gene expression. Drosophila roX2 and mammalian Xist lncRNAs, during dosage compensation, hyperactivate or repress expression of genes on X chromosome, respectively. Regulation of X-linked genes is accomplished through association of lncRNA with chromatin modifying proteins and subsequent spreading of these complexes and associated chromatin marks to the more distal regions of the chromatin. The state of chromatin marks at a given gene location has a direct influence on gene activity through regulation of compaction state of the chromatin fiber and binding of transcription factors. The extent of spreading therefore dictates, which genes will be subject to activation or repression. What more, regulation of X-linked genes was shown to play crucial role in both suppression and promotion of cancer formation (Chaligne et al., 2014, FEBS Lett, 588(15): 2514-2522; Chaligne et al., 2015, Genome research, 25(4): 488-503; Dunford et al., 2017, Nature genetics 49(1): 10-16). Therefore, knowing the precise localization of the lncRNA complexes is essential for understanding of spreading of chromatin-modifying complexes and the underlying gene expression changes.

Several RNA-centric techniques have been developed recently to study RNA association with chromatin. Global RNA interactions with DNA by deep sequencing (GRID-seq) utilizes proximity ligation to identify RNA fragments and their associated DNA sequences. Although, GRID-seq provides genome-wide view of RNA occupancy on chromatin, the main drawbacks are its low sensitivity for low expressed RNAs and a limited resolution. On the other side stand Capture Hybridization Analysis of RNA Targets (CHART), Chromatin Isolation by RNA Purification (ChIRP) and RNA Affinity Purification (RAP), collectively referred to as hybridization capture methods. Hybridization capture methods use a pool of biotinylated antisense oligonucleotides to specifically hybridize and isolate RNA of interest. However, a common weakness of these methods is frequent occurrence of unspecific off-target hybridization. This leads to low signal-to-noise ratios, which make interpretation of the data challenging and can lead to false negative or false positive identification of RNA-chromatin association sites.

Accordingly, there is a need for improved methods that permit rapid, sensitive, and accurate RNA capture. The present invention fulfills this need.

SUMMARY

In one embodiment, the invention relates to a method for identifying a binding partner of a nucleic acid molecule of interest comprising the steps of: a) contacting a complex comprising a target nucleic acid molecule with nucleic acid molecule comprising a duplex formed from hybridization of at least one protector oligonucleotide (PO) with at least one capture oligonucleotide (CO), wherein the CO comprises a 5' toehold region, a central region, wherein the central region comprises a nucleotide sequence that is complementary to a nucleotide sequence of a target nucleic acid molecule and further comprises at least one modification, and a 3' toehold region; and wherein the PO comprises a nucleotide sequence complementary to the central region and one of the 5' toehold region and the 3' toehold region of the CO, such that strand exchange occurs between the CO and the complex comprising a target nucleic acid molecule to form a CO:target complex; b) washing the CO:target complex; c) immunoprecipitating the CO:target complex; and d) eluting at least one component of the complex comprising the target nucleic acid molecule.

In one embodiment, the 5' toehold region CO comprises a nucleotide sequence that is complementary to a nucleotide sequence of a target nucleic acid molecule and wherein the 3' toehold region of the CO comprises a nucleotide sequence that is complementary to a nucleotide sequence of a PO.

In one embodiment, the 3' toehold region CO comprises a nucleotide sequence that is complementary to a nucleotide sequence of a target nucleic acid molecule and wherein the 5' toehold region of the CO comprises a nucleotide sequence that is complementary to a nucleotide sequence of a PO.

In one embodiment, the CO further comprises a tag for affinity purification.

In one embodiment, the CO comprises at least one locked nucleic acid (LNA) modification in the central region.

In one embodiment, the PO is an RNA oligonucleotide. In one embodiment, the CO:PO complex comprises a RNA:DNA hybrid molecule comprising a ssDNA overhang which serves as one of a 5' toehold region and a 3'toehold region.

In one embodiment, the ssDNA overhang comprises at least 4 nucleotides.

In one embodiment, step d) comprises contacting the CO:target complex with an eluction oligonucleotide (EO), wherein the EO comprises a nucleotide sequence complementary to the full length of the CO. In one embodiment, the EO is an RNA oligonucleotide. In one embodiment, the EO comprises at least one 2' O-methylated nucleoside.

In one embodiment, the target nucleic acid molecule is crosslinked to at least one of a nucleic acid molecule and a protein, and step d) further comprises a step of reversing the crosslinks.

In one embodiment, the target nucleic acid molecule is in a complex with at least one nucleic acid molecule the method further comprises the steps of: e) ligating at least one adaptor molecule to an eluted nucleic acid molecule, f) amplifying the eluted nucleic acid molecule, and g) sequencing the amplified products.

In one embodiment, the invention relates to a CO for use in a method for identifying a binding partner of a nucleic acid molecule of interest comprising a 5' toehold region, a central region, wherein the central region comprises a nucleotide sequence that is complementary to a nucleotide sequence of a target nucleic acid molecule and further comprises at least one modification, and a 3' toehold region. In one embodiment, the 5' toehold region CO comprises a nucleotide sequence that is complementary to a nucleotide sequence of a target nucleic acid molecule and wherein the 3' toehold region of the CO comprises a nucleotide sequence that is complementary to a nucleotide sequence of a PO. In one embodiment, the 3' toehold region CO comprises a nucleotide sequence that is complementary to a nucleotide sequence of a target nucleic acid molecule and wherein the 5' toehold region of the CO comprises a nucleotide sequence that is complementary to a nucleotide sequence of a PO. In one embodiment, the CO is linked to a tag for affinity purification. In one embodiment, the CO comprises at least one locked nucleic acid (LNA) modification in the central region. In one embodiment, each of the 5' toehold region and the 3' toehold region comprises at least 4 nucleotides.

In one embodiment, the invention relates to a PO for use in a method for identifying a binding partner of a nucleic acid molecule of interest comprising a nucleotide sequence complementary to the central region and one of a 5' toehold region and a 3' toehold region of a CO. In one embodiment, the PO is an RNA oligonucleotide.

In one embodiment, the invention relates to a EO for use in a method for identifying a binding partner of a nucleic acid molecule of interest comprising a nucleotide sequence complementary to the full length sequence of a CO. In one embodiment, the EO is an RNA oligonucleotide. In one embodiment, the EO comprises at least one 2' O-methylated nucleoside.

In one embodiment, the invention relates to a kit comprising at least one of a CO and a PO for use in a method for identifying a binding partner of a nucleic acid molecule of interest. In one embodiment, the kit further comprises at least one EO.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A depicts a schematic diagram of the toehold hybridization design. Toehold oligonucleotides consist of a pre-hybridized capture oligonucleotide (CO) and a shorter protecting oligonucleotide (PO). Annealing to RNA target is reversible and happens through a strand exchange reaction. Formaldehyde cross-linked and sheared chromatin is incubated with biotinylated CO that will hybridize to the target RNA. Complexes are captured with streptavidinmbeads, washed to remove background and eluted with proteinase K treatment. FIG. 1B depicts a schematic diagram demonstrating that when the LNA modifications are limited only to the central region of CO and RNA is used as PO, the only parameters needed to calculate free energy of the reaction are hybridization energies of both toeholds. FIG. 1C depicts a CO:PO pair against roX2 lncRNA. PO is made of RNA and the central region of CO contains LNA (capital letters). FIG. 1D depicts the results of an exemplary experiment in which roX2 RNA was incubated with pre-hybridized CO:PO pairs and resolved on native gel. FIG. 1E depicts the results of an exemplary experiment in which RNA-CO hybrids were washed with 10 mM NaCl, 10 mM HEPES pH 7.7, 2 mM EDTA, 1 mM EGTA, 0.2% SDS at indicated temperature. FIG. 1F depicts a schematic diagram showing that excess elution oligonucleotide (EO) releases target RNA and associated molecules from CO. FIG. 1G depicts exemplary results demonstrating the percentage of RNA displaced from the RNA:CO complex after a 3 minute incubation using an EO that is specific for the CO and a control EO.

FIG. 2A through FIG. 2D depict exemplary experimental results demonstrating optimization of the thCHART method. FIG. 2A depicts qPCR results of CHART experiment against roX2 lncRNA in Drosophila S2 cells using DNA, LNA or toehold version of LNA (thLNA) CO. FIG. 2B depicts qPCR results of CHART experiment against roX2 lncRNA in Drosophila S2 cells using DNA or toehold version of LNA (thLNA) CO. Complexes were washed with either mild (100 mM NaCl at 20° C.) or stringent conditions (10 mM NaCl at 50° C.). FIG. 2C depicts results showing the percentage of RNA enrichment of roX2 CHART done under stringent wash conditions using toehold LNA CO and elution either with proteinase K (thLNA) or with excess of EO (thCHART). FIG. 2D depicts results showing the percentage of DNA enrichment of roX2 CHART done under stringent wash conditions using toehold LNA CO and elution either with proteinase K (thLNA) or with excess of EO (thCHART).

FIG. 3A depicts an analysis of the enrichment of RNA using DNA, LNA or thCHART. FIG. 3B depicts experimental results demonstrating the percentage of reads that map to the roX2 gene. FIG. 3C depicts experimental results demonstrating the level of roX2 RNA enrichment.

FIG. 4A depicts exemplary fold enrichment tracks of reads aligned to the Drosophila genome (dm6). Reads with mapping quality <2 were removed. FIG. 4B depicts the number of reads mapped to Drosophila chromosomes. FIG. 4C depicts an analysis in which the number of aligned reads were normalized to the length of the respective chromosome and the enrichment score was calculated as a ration between signal of chromosome X and the rest of the genome. FIG. 4D depicts an analysis in which RNA-seq reads were aligned to the Drosophila transcriptome and the reads aligned to roX2 gene were normalized to the total number of reads. Enrichment score was calculated as a ratio between normalized roX2 reads in sample and input. a—(Simon et al., 2013, Nature, 504:465-469) b—(Chu et al., 2011, Mol Cell, 44:667-678), c—(Alekseyenko et al., 2008, Cell 134(4): 599-609).

FIG. 5A through FIG. 5G depict exemplary experimental results demonstrating that thCHART does not suffer from sequence-dependent signal variability. FIG. 5A depicts an analysis of the enrichment across the genome using CO1 and CO2. FIG. 5B depicts the number of reads mapped to Drosophila chromosomes. FIG. 5C depicts an analysis in which the number of aligned reads were normalized to the length of the respective chromosome and the enrichment score was calculated as a ratio between signal of chromosome X and the rest of the genome. FIG. 5D depicts an analysis of the correlation of 'odd' and 'even' ChIRP datasets. FIG. 5E depicts an analysis of the correlation of thCHART CO1 and thCHART CO2 datasets. FIG. 5F depicts an analysis of the correlation of ChIRP odd and thCHART CO1+2 datasets. FIG. 5G depicts an analysis of the correlation of CHART and thCHART CO1+2 datasets.

FIG. 6A through FIG. 6C depict exemplary experimental results demonstrating that thCHART can be used for RNAs of various lengths that associate with chromatin. FIG. 6A depicts an analysis of the sequencing results using a CO against repC of mouse Xist. FIG. 6B depicts the number of reads mapped to mouse chromosomes. FIG. 6C depicts an analysis in which the number of aligned reads were normalized to the length of the respective chromosome and the enrichment score was calculated as a ratio between signal of chromosome X and the rest of the genome.

FIG. 7A through FIG. 7E depict exemplary experimental results demonstrating that the enhanced data quality produced by thCHART improves knowledge about lncRNA and chromatin modifying complexes localization. FIG. 7A depicts exemplary experimental results demonstrating that CHART, ChIRP and thCHART detect MSL complex peaks found at well-defined chromatin entry sites and further thCHART can detect areas outside of chromatin entry sites that carry hallmarks of active genes (H3K36me3 chromatin mark) or active transcription. FIG. 7B depicts an analysis of the cumulative mean of signal intensity for CHART, ChIPR and thCHART. FIG. 7C depicts the percentage of MSL signal coverage for PolII transcribed genes. FIG. 7D depicts the percentage of MSL signal coverage for genes having a H3K36me3 chromatin mark. FIG. 7E depicts the percentage of MSL signal coverage for transcribed genes.

FIG. 8A depicts a comparison of roX2 signal intensity between heat-shock treated and untreated cells. FIG. 8B depicts an analysis of the correlation of heat shock and control datasets. FIG. 8C depicts an analysis of the correlation of DRB treated and control datasets.

FIG. 9A depicts the results of exemplary experiments in which RNA-capture oligonucleotide hybrids were immobilized on magnetic beads and washed with 35% Formamide at the indicated temperatures. FIG. 9B depicts the results of exemplary experiments in which immobilized hybrids were sequentially washed with 8 M Urea, 6 M Guanidinium chloride and 35% Formamide.

DETAILED DESCRIPTION

Figure 1A:
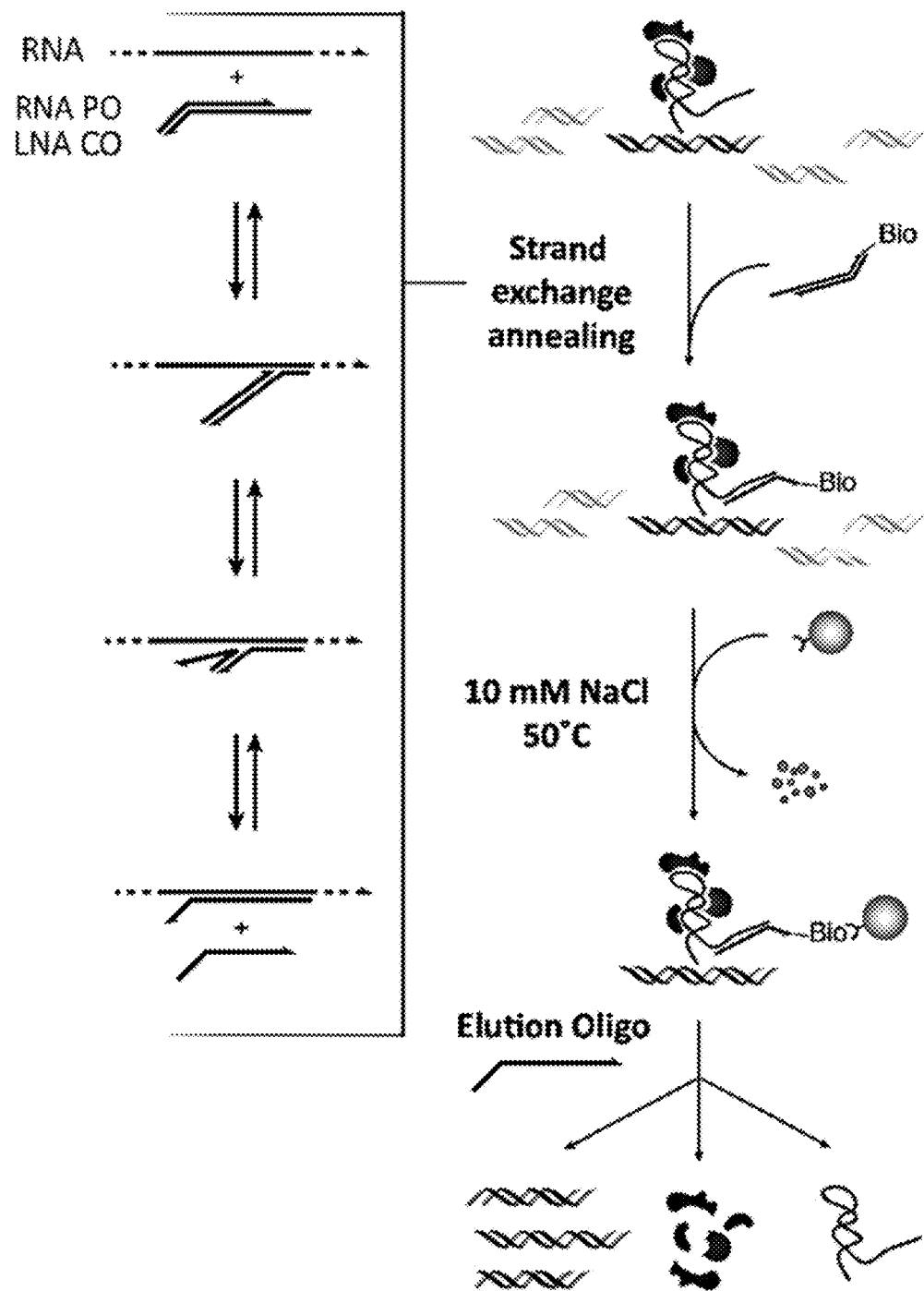
FIG. 1A through FIG. 1G depict exemplary experimental results demonstrating that the toehold design allows specific hybridization of locked nucleic acid (LNA)-containing capture oligonucleotides.

The present invention relates to methods and compositions for detecting the sequence or identity of an interacting partner of a target nucleic acid molecule. In one embodiment, the methods of the invention have been developed to reduce the signal-to-noise ratio of chromatin-association data for any given endogenous RNA. The invention is based, in part, on the development of a new hybridization capture method called ToeHold CHART (thCHART) that uses a toehold-mediated strand exchange reaction to specifically hybridize LNA-containing antisense oligonucleotide to a target RNA molecule.

In one embodiment, the thCHART method of the invention comprises the use of a capture oligonucleotide (CO) having two toehold regions and a central region that comprises at least one modification. In one embodiment, prior to contact with a target nucleic acid molecule, the CO is bound by a protector oligonucleotide (PO) which is complementary to one toehold region and the central region of the CO, leaving a single stranded overhang region of the CO which serves as a toehold for binding to the target nucleic acid molecule. Upon contact with the target nucleic acid molecule, a strand exchange reaction occurs in which the first toehold and central region of the CO become bound to the target nucleic acid molecule and the PO becomes dissociated from the CO. The formation of a CO:target complex results in the exposure of the second toehold of the CO, which is complementary to a region of the PO, but is not complementary to a region of the target nucleic acid molecule.

In one embodiment, the CO comprises a tag, allowing for affinity purification or immunoprecipitation of the CO:target complex. Immunoprecipitaiton of the CO:target complex includes immunoprecipitation of the target nucleic acid molecule and any binding partner associated therewith. Therefore, in one embodiment, immunoprecipitation of the CO:target complex includes immunoprecipitation of a target nucleic acid molecule and one ore more of a crosslinked chromatin fragment and a crosslinked protein.

In one embodiment, the thCHART method of the invention comprises contacting an immunoprecipitated CO:target complex with an elution oligonucleotide (EO) comprising a nucleotide sequence complementary to the CO. Upon contact with the CO:target complex, a strand exchange reaction occurs in which the second toehold, central region, and first toehold of the CO become bound to the EO and the target complex is eluted. The exposure of the second toehold of the CO promotes dissociation of the CO:target complex in the presence of the EO.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "arrays," "microarrays," and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate. Microarrays can be prepared and used by a number of methods, including those described in U.S. Pat. No. 5,837,832 (Chee et al.), PCT application WO95/11995 (Chee et al.), Lockhart, D. J. et al. (Nat. Biotech. 14:1675-1680, 1996) and Schena, M. et al. (Proc. Natl. Acad. Sci. 93:10614-10619, 1996), all of which are incorporated herein in their entirety by reference. In other embodiments, such arrays can be produced by the methods described by Brown et al., U.S. Pat. No. 5,807,522.

The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, an "adaptor" of the present invention means a piece of nucleic acid that is added to a nucleic acid of interest, e.g., the polynucleotide. Two adaptors of the present invention are preferably ligated to the ends of a DNA fragment cross-linked to a polypeptide of interest, with one adaptor on each end of the fragment. Adaptors of the present invention can comprise a primer binding sequence, a random nucleotide sequence, a barcode, or any combination thereof.

An affinity label, as the term us used herein, refers to a moiety that specifically binds another moiety and can be used to isolate or purify the affinity label, and compositions to which it is bound, from a complex mixture. One example of such an affinity label is a member of a specific binding pair (e.g., biotin:avidin, antibody:antigen). The use of affinity labels such as digoxigenin, dinitrophenol or fluorescein, as well as antigenic peptide 'tags' such as polyhistidine, FLAG, HA and Myc tags, is envisioned.

"Amplification," as used herein, refers to any in vitro process for increasing the number of copies of a nucleotide sequence or sequences, i.e., creating an amplification product which may include, by way of example additional target molecules, or target-like molecules or molecules complementary to the target molecule, which molecules are created by virtue of the presence of the target molecule in the sample. These amplification processes include but are not limited to polymerase chain reaction (PCR), multiplex PCR, Rolling Circle PCR, ligase chain reaction (LCR) and the like, in a situation where the target is a nucleic acid, an amplification product can be made enzymatically with DNA or RNA polymerases or transcriptases. Nucleic acid amplification results in the incorporation of nucleotides into DNA or RNA. As used herein, one amplification reaction may consist of many rounds of DNA replication. PCR is an example of a suitable method for DNA amplification. For example, one PCR reaction may consist of 2-40 "cycles" of denaturation and replication.

"Amplification products," "amplified products" "PCR products" or "amplicons" comprise copies of the target sequence and are generated by hybridization and extension of an amplification primer. This term refers to both single stranded and double stranded amplification primer extension products which contain a copy of the original target sequence, including intermediates of the amplification reaction.

As used herein, an "antibody" encompasses naturally occurring immunoglobulins, fragments thereof, as well as non-naturally occurring immunoglobulins, including, for example, single chain antibodies, chimeric antibodies (e.g., humanized murine antibodies), heteroconjugate antibodies (e.g., bispecific antibodies). Fragments of antibodies include those that bind antigen, (e.g., Fab', F(ab')2, Fab, Fv, and rIgG). See, e.g., Pierce Catalog and Handbook, 1994-1995 (Pierce Chemical Co., Rockford, Ill.); Kuby, J., Immunology, 3rd Ed., W. H. Freeman & Co., New York (1998). The term "antibody" further includes both polyclonal and monoclonal antibodies.

"Appropriate hybridization conditions" as used herein may mean conditions under which a first nucleic acid sequence (e.g., primer, etc.) will hybridize to a second nucleic acid sequence (e.g., target, etc.), such as, for example, in a complex mixture of nucleic acids. Appropriate hybridization conditions are sequence-dependent and will be different in different circumstances. In one embodiment, an appropriate hybridization conditions may be selective or specific wherein a condition is selected to be about 5-10° C. lower than the thermal melting point ($T_m$) for the specific sequence at a defined ionic strength and pH. In one embodiment, an appropriate hybridization condition encompasses hybridization that occurs over a range of temperatures from more to less stringent. In one embodiment, a hybridization range may encompass hybridization that occurs from 98° C. to 50° C. According to the invention, such a hybridization range may be used to allow hybridization of the primers of the invention to target sequences with reduced specificity, for the purposes of amplifying a broad range of nucleic acid molecules with a single set of primers.

A "barcode", as used herein, refers to a nucleotide sequence that serves as a means of identification for sequenced polynucleotides of the present invention. Barcodes of the present invention may comprise at least 4 random bases, such as 5, 6, 7, 8, 9, 10, 11, 12, 13, 14, 15, 16, 17, 18, 19, 20 or more bases in length. Alternativley, or in addition to the random nucleotides, the barcode may have three or more fixed bases, 4, 5, 6, 7, 8, 9, 10, 11, 12, 13, 14, 15, 16, 17, 18, 19, 20 or more bases in length. In some embodiments, both random and fixed bases are used as barcodes. For example, a barcode can be composed of 5 random bases and 4 fixed bases. Methods for designing barcodes are known in the art. See, e.g., Bystrykh (2012) PLoS ONE, 7(5): e36852; Mir et al., (2013) PLoS ONE, 8(12): e82933.

As used herein, "binding" means an association interaction between two molecules, via covalent or non-covalent interactions including, but not limited to, hydrogen bonding, hydrophobic interactions, van der Waals interactions, and electrostatic interactions. Binding may be sequence specific or non-sequence specific. Non-sequence specific binding may occur when, for example, a polypeptide of interest (i.e. a histone) binds to a polynucleotide of any sequence. Specific binding may occur when, for example, a polypeptide of interest (i.e. a transcription factor) binds oredominantly to a highly restricted sequence of nucleotides.

Chromatin is the compacted structure of genomic DNA present in the nucleus of most eukaryotic cells. It comprises DNA and a plurality of DNA-binding proteins as well as certain RNAs. The term 'chromatin' derives from the readiness of this cellular material to hold stain with certain chemical dyes (chromaticity). Chromatin is primarily comprised of DNA associated with histone proteins that together form a basic nucleosomal structure. The nucleosome comprises an octet of histone proteins around which is wound a stretch of double stranded DNA 146 by in length. Histones H2A, H2B, H3 and H4 are part of the nucleosome while histone H1 can act to link adjacent nucleosomes together into a higher order structure. Assembly into higher order structures allows for greater packing, or condensation of the DNA. Chromatin is often referred to as occurring in two main states, euchromatin and heterochromatin, corresponding to uncondensed actively transcribed DNA and condensed DNA respectively. Many further polypeptides, RNAs and protein complexes interact with the nucleosome and the histones in order to mediate transition between the euchromatic and heterochromatic states. The identity and functional activity of many of these crucially important chromatin associated proteins and complexes is presently unknown.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

As used herein, "dNTPs" refers to a mixture of different deoxyribonucleotide triphosphates: deoxyadenosine triphosphate (dATP), deoxycytidine triphosphate (dCTP), deoxyguanosine triphosphate (dGTP) and deoxythymidine triphosphate (dTTP).

"Fragment" as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. When comparing DNA and RNA, thymine (T) and uracil (U) may be considered equivalent. Identity may be performed manually or by using a computer sequence algorithm such as BLAST or BLAST 2.0.

As used herein, "immunoprecipitating", and grammatical variations thereof, refers to a protocol in which polypeptides, such as antibodies, that specifically bind target polypeptides, are utilized to separate the target polypeptides and the substances that are physically linked to such polypeptides (such as a polynucleotide) from a plurality of other cellular materials. For example, cross-linked polypeptide-polynucleotide complexes of the present invention may be separated from other cellular materials by applying a cell extract to an affinity purification matrix, wherein the affinity purification matrix comprises an antibody specific for the target polypeptide linked to a substrate. The target polypeptide-polynucleotide complexes will bind to the antibody and may later be eluted, thereby separating the target polypeptide-polynucleotide complexes from other cellular materials. Detailed conditions for immunoprecipitation are disclosed herein and are also known in the art and may be found in e.g., Bonifacino et al., (2016) Curr Protoc Cell Biol, 71:7.2.1-7.2.24.

"Nucleic acid" or "oligonucleotide" or "polynucleotide" or "nucleic acid fragment" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence. Thus, a nucleic acid also encompasses a probe that hybridizes under appropriate hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

As used herein, a "polypeptide of interest" may be any polypeptide for which said polypeptide's genomic binding regions are sought. It is envisioned that a polypeptide of the present invention may include full length proteins and protein fragments. While the methods of the present invention may be utilized not only to determine at least one region of a genome at which a polypeptide of interest binds, they may also be utilized to determine if a polypeptide binds to a genome at all. The polypeptide of interest may selected from the group consisting of a transcription factor, a polymerase, a nuclease, and a histone.

A "polypeptide complex" as used herein, is intended to describe proteins and polypeptides that assemble together to form a unitary association of factors. The members of a polypeptide complex may interact with each other via non-covalent or covalent bonds. Typically members of a polypeptide complex will cooperate to enable binding either to DNA or to polypeptides and proteins already associated with or bound to DNA (i.e. chromatin). Chromatin associated polypeptide complexes may comprise a plurality of proteins and/or polypeptides which each serve to interact with other polypeptides that may be permanently associated with the complex or which may associate transiently, dependent upon cellular conditions and position within the cell cycle. Hence, particular polypeptide complexes may vary in their constituent members at different stages of development, in response to varying physiological conditions or as a factor of the cell cycle. By way of example, in animals, polypeptide complexes with known chromatin remodelling activities include Polycomb group gene silencing complexes as well as Trithorax group gene activating complexes.

"Primer" as used herein refers to a single-stranded oligonucleotide or a single-stranded polynucleotide that is extended on its 3' end by covalent addition of nucleotide monomers during amplification. Nucleic acid amplification often is based on nucleic acid synthesis by a nucleic acid polymerase. Many such polymerases require the presence of a primer that can be extended to initiate such nucleic acid synthesis.

As used herein, "purifying" the polynucleotides of the present invention refers to a process well known to those of skill in the art in which polynucleotides are substantially separated from other components in a sample, including, but not limited to, polypeptides of interest.

As used herein, "sample" or "test sample," may refer to any source used to obtain nucleic acids for examination using the compositions and methods of the invention. A test sample is typically anything suspected of containing a target sequence. Test samples can be prepared using methodologies well known in the art such as by obtaining a specimen from an individual and, if necessary, disrupting any cells contained thereby to release genomic nucleic acids. These test samples include biological samples which can be tested by the methods of the present invention described herein and include human and animal cells, tissues and body fluids such as whole blood, serum, plasma, cerebrospinal fluid, sputum, bronchial washing, bronchial aspirates, urine, lymph fluids and various external secretions of the respiratory, intestinal and genitourinary tracts, tears, saliva, milk, white blood cells, myelomas, buccal cells, cervicovaginal cells, epithelial cells from urine, fetal cells, or any cells present in tissue obtained by biopsy and the like; biological fluids such as cell culture supernatants; tissue specimens which may be fixed; and cell specimens which may be fixed.

Any DNA sample may be used in practicing the present invention, including without limitation eukaryotic, prokaryotic and viral DNA. In one embodiment, the target DNA represents a sample of genomic DNA isolated from a patient. This DNA may be obtained from any cell source, tissue source, or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, semen and tissue exudates at the site of infection or inflammation. DNA is extracted from the cell source, tissue source, or body fluid using any of the numerous methods that are standard in the art. It will be understood that the particular method used to extract DNA will depend on the nature of the source.

As used herein, "reverse cross-linking" the polypeptide-polynucleotide complex refers to a protocol well known to those of skill in the art in which a protease (i.e., Protease K), heat, or both are utilized to break the covalent linkages between the polypeptides of interest and the polynucleotide fragments.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of about 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under appropriate hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%,or 99% over a region of about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

As used herein, a "substrate" is a solid platform on which antibodies used in immunoprecipitation are bound.

A "target nucleic acid" as the term is used herein, refers to a nucleic acid to which another nucleic acid binds in the context of the cellular environment. Typically such binding is through complementarity of the respective nucleic acid sequences.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present technique is referred to as toehold Capture Hybridization Analysis of RNA Targets (thCHART), a hybridization-based strategy to map genome-wide binding sites for endogenous RNAs (including ncRNAs and lncRNAs). thCHART involves contacting a target nucleic acid molecule with a capture oligonucleotide having a region that is complementary to the target nucleic acid molecule to purify the target nucleic acid molecule, and molecules that are crosslinked to it, from cellular extracts. A schematic diagram of thCHART is provided in FIG. 1A and FIG. 1B. thCHART uses a capture oligonucleotide (CO) having at least one toehold region and further comprising at least one LNA. In one embodiment, the CO comprises three regions: 1) a first toehold region which comprises a nucleotide sequence complementary to a nucleotide sequence of a target nucleic acid molecule, but not complementary to a nucleotide sequence of a protector oligonucleotide (PO), 2) a central region comprising a nucleotide sequence that is complementary to a nucleotide sequence of a target nucleic acid molecule, and also complementary to a nucleotide sequence of a PO and further comprises at least one LNA, and 3) a second toehold region which is complementary to a nucleotide sequence of a PO and is also complementary to a nucleotide sequence of an elution oligonucleotide (EO), but is not complementary to a nucleotide sequence of a target nucleic acid molecule. In one embodiment, the CO is complexed to a protector oligonucleotide (PO) which results in the formation of a nucleic acid molecule in which there is a double stranded region formed of the CO:PO complex and a single stranded region compising the first toehold region of the CO. In the presence of a target nucleic acid molecule, the first toehold region of the CO serves to promote strand exchange between the CO and the target nucleic acid molecule to form a nucleic acid molecule in which there is a double stranded region formed of the CO:target complex and a single stranded region compising the second toehold region of the CO. In one embodiment, the second toehold region of the CO promotes strand exchange between the CO and the PO to re-generate a CO:PO complex nucleic acid molecule. In one embodiment, the second toehold region of the CO promotes strand exchange between the CO and the EO to form a CO:EO complex nucleic acid molecule.

In various embodiments, the first toehold region may be the 5' end or the 3' end of the CO. Similarly, the second toehold region may be the 5' end or the 3' end of the CO. Therefore, in one embodiment, the first toehold, having a nucleotide sequence complementary to the target nucleic acid sequence but not the PO, is on the 5' end of the CO and the second toehold, having a nucleotide sequence complementary to the PO but not the target nucleic acid sequence, is on the 3' end of the CO. In another embodiment, the first toehold, having a nucleotide sequence complementary to the target nucleic acid sequence but not the PO, is on the 3' end of the CO and the second toehold, having a nucleotide sequence complementary to the PO but not the target nucleic acid sequence, is on the 5' end of the CO.

In one embodiment, thCHART allows the identification of the genomic loci where RNAs are bound to chromatin. This technique is generally applicable; thCHART is capable of enriching different RNAs from different organisms.

Although the invention is described in terms of a modified CHART method, it should be understood that the methods of the invention can be applied to other immunoprecipitation-based next-Gen sequencing assays including, but not limited to, Protein Interaction Profile Sequencing (PIP-seq), ChIP-exo, MNase ChIP-seq, Chem-seq, RNA-seq and PB-seq, in which a toehold CO can replace an antibody for capture of a target nucleic acid molecule. In addition, it should be understood that the term immunoprecipitation is used to include other forms of affinity purification and therefore the methods of the invention can be applied to methods in which proteins of interest are precipitated using affinity purification methods, including, but not limited to, precipitation of a protein of interest using a purification tag, or through enzymatic modification (e.g., biotinylation). Exemplary purification tags include, but are not limited to, chitin binding protein (CBP), maltose binding protein (MBP), Strep-tag, glutathione-S-transferase (GST), poly(His) tag, FLAG-tag and epitope tags which include, but are not limited to V5-tag, Myc-tag, HA-tag and NE-tag.

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Chromatin capture methods are known in the art and are described in Simon (2013) Curr Protoc Mol Biol, Chapter 21:Unit 21.25; Sexton et al., (2016) Methods Mol Biol, 1480:87-97; and Chu et al., (2016) Methods Mol Biol, 1480:115-23, as well as in methodology treatises such as Chromatin Immunoprecipitation Assays: Methods and Protocols (Methods in Molecular Biology) by Philippe Collas, 1st edition, 2009, Humana Press, Totowa, N.J.; and DNA-Protein Interactions (Methods in Molecular Biology) by Tom Moss (ed.) and Benoit Leblanc (ed.), 3rd edition, 2009, Humana Press, Totowa, N.J.

Any type of cell or reconstituted protein-nucleic acid complex can be used in the thCHART assays of the invention. Any sample from which nucleic acid molecules can be isolated can be used in the assay system. Indeed, in certain instances it may be advantageous to use different sample types, e.g., blood, cancer cells, saliva, and formalin-fixed paraffin embedded (FFPE) samples.

The assays are also applicable in the absence of crosslinking, as long as the protein remains bound to the nucleic acid. A population of cells (or in vitro assembled complexes) is incubated with a chemical crosslinking reagent such as formaldehyde, which crosslinks proteins to each other and to nucleic acids such as DNA and RNA. Any suitable crosslinking reagent can be used. In one embodiment, the crosslinker is used to preserve in vivo protein-nucleic acid interactions during the stringent work-up conditions that are meant to diminish nonspecific contamination. The crosslinking reaction is almost instantaneous, and provides a snapshot of the protein-nucleic acid interactions taking place in the cell. The next step of the assay requires cell disruption and washing of the insoluble chromatin to remove non-chromatin soluble proteins. In one embodiment, the chromatin is then fragmented and solubilized using sonication. Sonication randomly shears DNA to a size range of about 300 by in yeast and 0.5-1 kb in vertebrates, although more intense sonication can create smaller fragment sizes.

In one embodiment the thCHART assays of the invention include purification a complex formed between chromatin and a chromatin binding molecule. In one embodiment, a chromatin binding molecule is a target nucleic acid molecule. In one embodiment, a chromatin binding molecule is associated with a target nucleic acid molecule. Therefore, the thCHART assay can be used to identify a direct or indirect interaction between chromatin and a target nucleic acid molecule. Chromatin binding molecules include, but are not limited to, an RNA molecule, a ribonucleoprotein (RNP) complex, and a nucleic acid binding protein. In one embodiment, a target nucleic acid molecule is an RNA molecule. RNA molecules include, but are not limited to, an mRNA molecule, a ncRNA molecule, a lncRNA molecule, a siRNA, a shRNA, a snoRNA, a U-RNA, a Y RNA, a snRNA, a srRNA, a sgRNA, a vault RNA, a LINE RNA, a circRNA, polyadenylated (poly(A)) RNA or a microRNA molecule. In one embodiment, the method of purification of a complex formed between chromatin and a chromatin binding molecule takes the form of affinity purification where an affinity tag on the CO is used to selectively pull out of solution the CO bound to a target nucleic acid molecule, along with any nucleic acid molecule or protein with which it is associated or crosslinked to. Buffer and wash conditions are of sufficient stringency (e.g., low sodium wash solutions at increased temperature) that retention of nucleic acid contaminants that have not been directly or indirectly crosslinked to the target protein are diminished.

In various embodiments of the thCHART assays of the invention, the ends of the fragmented chromatin are ligated or annealed to a known DNA sequence such as a DNA adaptor or barcode following crosslink reversal to allow for sequencing of the eluted chromatin fragment.

In various embodiments, the adapters that are added to the 5' and/or 3' end of a nucleic acid can comprise a universal sequence. A universal sequence is a region of nucleotide sequence that is common to, i.e., shared by, two or more nucleic acid molecules. Optionally, the two or more nucleic acid molecules also have regions of sequence differences. Thus, for example, the 5' adapters can comprise identical or universal nucleic acid sequences and the 3' adapters can comprise identical or universal sequences. A universal sequence that may be present in different members of a plurality of nucleic acid molecules can allow the replication or amplification of multiple different sequences using a single universal primer that is complementary to the universal sequence.

In one embodiment, one or more nucleic acid molecules or proteins are bound but not crosslinked to the target nucleic acid molecule, therefore the thCHART method of the invention includes a step of eluting the bound nucleic acid molecules. Any procedures known in the art that disrupt protein:nucleic acid complexes or nucleic acid duplexes and elute the nucleic acid molecules may be employed.

In one embodiment, the thCHART method of the invention includes a step to reverse the crosslink of a nucleic acid molecule complex, and eluting the complex components. In various embodiments, the complex components may be DNA molecules, RNA molecules, proteins, peptides, or a combination thereof. Any procedures known in the art may be employed that reverse the crosslinks and elute the complex components. An exemplary method for reversal of crosslinkes includes incubation of the immunoprecipitated chromatin fragments at a temperature of at least 15° C., at least 20° C., at least 25° C., at least 30° C., at least 35° C., at least 40° C., at least 45° C., at least 50° C., at least 55° C., at least 60° C., or at least 65° C. for at least 30 minutes, at least 1 hour, at least 2, hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24, or for more than 24 hours. An alternative exemplary method for reversal of crosslinkes includes incubation of the immunoprecipitated chromatin fragments at a temperature of at least 80° C., at least 85° C., at least 90° C., or at least 95° C. for at least 10 minutes, at least 15 minutes, at least 20 minutes, at least 25 minutes, at least 30 minutes, or for more than 30 minutes. In one embodiment, the elution and/or crosslink reversal is performed in the presence of one or more of Proteinase K and RNAse. In one embodiment, the nucleic acid molecules are incubated in the presence of one or more of Proteinase K and RNAse prior to or subsequent to elution and/or crosslink reversal.

In one embodiment, the methods of the invention include one or more purification steps. Any procedures known in the art may be employed for purifying a nucleic acid molecule or protein. Methods for purifying a nucleic acid molecule include, but are not limited to, ethanol purification, column-based purification methods, gel-based purification methods, and magnetic bead based purification methods. Methods for purifying a protein or peptide include, but are not limited to, immunoprecipitation, centrifugation, chromatography, and high-performance liquid chromatography (HPLC).

In one embodiment, a thCHART sequencing library is generated using the eluted nucleic acid molecules. In one embodiment, the eluted nucleic acid molecules are amplified prior to sequencing. Any procedures known in the art may be employed that amplify the nucleic acid molecules. An exemplary method for amplification of nucleic acid molecules is using PCR.

In some embodiments, one or more thCHART libraries are sequenced using single-molecule DNA sequencing (e.g., using true single molecule or clusters of identical clones) to identify the nucleotide sequences of the individual DNA molecules. In various embodiments, the sequencing can be accommodated by Illumina, Applied Biosystems, Roche, and other deep sequencing technologies. Hybridization-based detection platforms could also be used but provide less resolution.

In some embodiments, multiple thCHART libraries are prepared in parallel and then pooled to generate a high throughput assay. For example, parallel assays may be carried out in a multi-well plate, such as a 96-well plate or a 384 well plate. The number of pooled samples is not necessarily limited as the limiting factors are 1) the number of sequence specific barcodes and 2) the number of sequencing reads desired per sample for a given sequencing platform. Therefore, the method may be extended to include more samples at a cost of reduced sequencing read coverage per sample.

In one embodiment, the identity of one or more eluted protein or peptide molecule is determined. Methods for identifying proteins or peptides are well known in the art and include, but are not limited tos spectrometry methods, such as HPLC, mass spectrometry (MS), liquid chromatography-mass spectrometry (LC/MS), Enzyme-linked immunosorbent assay (ELISA), immunoprecipitation, immunoelectrophoresis, Western blot and immunostaining.

CO Oligonucleotide

In one embodiment, the invention provides a CO oligonucleotide for use in thCHART. In various embodiments, the CO is an RNA oligonucleotide, a DNA oligonucleotide, a modified RNA oligonucleotide or a modified DNA oligonucleotide.

In one embodiment, the CO comprises three regions: 1) a first toehold region which comprises a nucleotide sequence complementary to a nucleotide sequence of a target nucleic acid molecule, but not complementary to a nucleotide sequence of a PO, 2) a central region comprising a nucleotide sequence that is complementary to a nucleotide sequence of a target nucleic acid molecule, and also complementary to a nucleotide sequence of a PO, and 3) a second toehold region which is complementary to a nucleotide sequence of a PO and is also complementary to a nucleotide sequence of an EO, but is not complementary to a nucleotide sequence of a target nucleic acid molecule. In one embodiment, the first toehold region of the CO comprises a nucleotide region at an end of the CO. In one embodiment, the first toehold region comprises at least 2, 3, 4, 5, 6, 7, 8, 9, 10 or more than 10 nucleotides of the 5' end of the CO. In one embodiment, the first toehold region comprises at least 2, 3, 4, 5, 6, 7, 8, 9, 10 or more than 10 nucleotides of the 3' end of the CO.

In one embodiment, the second toehold region of the CO comprises a nucleotide region at an end of the CO. In one embodiment, the second toehold region comprises at least 2, 3, 4, 5, 6, 7, 8, 9, 10 or more than 10 nucleotides of the 5' end of the CO. In one embodiment, the second toehold region comprises at least 2, 3, 4, 5, 6, 7, 8, 9, 10 or more than 10 nucleotides of the 3' end of the CO.

In one embodiment, the first toehold region, or the targeting toehold region, comprises the same number of nucleotides as the second toehold region, or the dissociation toehold region. In one embodiment, the targeting toehold region comprises at least 2, 3, 4, 5, 6, 7, 8, 9, 10 or more than 10 more nucleotides than the dissociation toehold region. In one embodiment, the targeting toehold region comprises at least 2, 3, 4, 5, 6, 7, 8, 9, 10 or more than 10 fewer nucleotides than the dissociation toehold region.

In one embodiment, the central region of the CO comprises a nucleotide region between the 5' toehold region and the 3' toehold region. In one embodiment, the central region comprises at least 1, 2, 3, 4, 5, 6, 7, 8, 9, 10, 11, 12, 13, 14, 15, 16, 17, 18, 19 20 or more than 20 nucleotides between the 5' toehold region and the 3' toehold region.

In one embodiment, at least one modification is included in a central region of the CO, but not in a toehold region. Desirable modifications are described, for example, in U.S. Patent Publication Nos. 20070213292, 20060287260, 20060035254, 20060008822, and 2005028824, each of which is hereby incorporated by reference in its entirety. For increased binding affinity to the target, the single-stranded oligonucleotide agents featured in the disclosure can include 2'-O-methyl, 2'-fluorine, 2'-O-methoxyethyl, 2'-O-aminopropyl, 2'-amino, and/or phosphorothioate linkages. Inclusion of LNA, ethylene nucleic acids (ENA), e.g., 2'-4'-ethylene-bridged nucleic acids, peptide nucleic acids (PNA), and certain nucleotide modifications can also increase binding affinity to the target.

In various embodiments, the CO comprises at least 1, 2, 3, 4, 5, 6, 7, 8, 9, 10 or more than 10 modifications in the central region. In one embodiment, the at least one modification is a LNA. Therefore, in one embodiment, the CO comprises at least 1, 2, 3, 4, 5, 6, 7, 8, 9, 10 or more than 10 LNAs in the central region. In one embodiment, the CO comprises a LNA at the first nucleotide of the central region and at every second nucleotide thereafter, such that every other nucleotide of the central region is an LNA.

In one embodiment, the CO comprises, or is linked to, a ligand for affinity purification. For example, in one embodiment, the CO is biotinylated, allowing for capture and purification of the complexed CO:target molecules using streptavidin affinity purification methods.

PO Oligonucleotide

In one embodiment, the invention provides a PO oligonucleotide for use in thCHART. In various embodiments, the PO is an RNA oligonucleotide, a DNA oligonucleotide, a modified RNA oligonucleotide or a modified DNA oligonucleotide. In one embodiment, the PO is complementary to the 3' toehold region and central region of the CO, such that it can hybridize to and form a double stranded region with the CO, i.e., form a CO:PO complex. In one embodiment, the PO is an RNA molecule that hybridizes to a DNA CO to form a CO:PO complex comprising a RNA:DNA hybrid region through the central region and 3' toehold region of the CO and a 5' ssDNA region comprising the 5' toehold region of the CO.

EO Oligonucleotide

In one embodiment, the invention provides a EO oligonucleotide for use in thCHART. In various embodiments, the EO is an RNA oligonucleotide, a DNA oligonucleotide, a modified RNA oligonucleotide or a modified DNA oligonucleotide.

In one embodiment, the EO is complementary to the 5' toehold region, central region, and 3' toehold region of the CO, such that it can hybridize to the CO and form a double stranded CO:EO complex.

In one embodiment, the EO comprises at least one modification. Modifications can include, but are not limited to, 2'-O-methyl, 2'-fluorine, 2'-O-methoxyethyl, 2'-O-aminopropyl, 2'-amino, and/or phosphorothioate linkages, LNA, and ENA. In one embodiment, the modification is a 2' O-Methyl modification.

thCHART

The overall procedure for this method is depicted in the right hand column of FIG. 1A. In one embodiment, the method comprises the steps of: a) crosslinking a target nucleic acid molecule, b) contacting the crosslinked target nucleic acid molecule with a CO:PO nucleic acid molecule such that strand exchange occurs between the CO and the target nucleic acid molecule; c) washing the CO:target nucleic acid molecule complex at least once with a wash buffer to reduce non-specific complexes; d) immunoprecipitating the CO:target nucleic acid molecule in a complex with any crosslinked nucleic acid molecule(s) or protein(s), e) contacting the immunoprecipitated complex with at least one EO such that strand exchange occurs between the CO and EO to form a CO:EO complex and release the target complex from the CO, and f) reversing the crosslinks and eluting at least one nucleic acid molecule(s) and/or protein(s) that was complexed to the target nucleic acid molecule.

In one embodiment, the thCHART method of the invention further comprises ligating at least one adaptor molecule to the eluted nucleic acid molecule, performing PCR amplification of the ligated molecule, and sequencing the PCR amplified products. In one embodiment, the resulting nucleic acid molecule sample is used for high-throughput sequencing, using, for example, the Illumina/Solexa GAII, AB SOLiD system, Ion Torrent PGM, Ion Proton, Illumina MiSeq, Illumina HiSeq 2000 or 2500 and the like.

In one embodiment, the thCHART method of the invention further comprises analyzing one or more proteins. Methods for analysis of proteins are known in the art and include HPLC, mass spectrometry (MS), liquid chromatography-mass spectrometry (LC/MS), Enzyme-linked immunosorbent assay (ELISA), immunoprecipitation, immunoelectrophoresis, Western blot and immunostaining.

In one embodiment, in step a), cells are crosslinked with formaldehyde and lysed. The crosslinked chromatin molecules are then fragmented prior to step b). In one embodiment, the chromatin is fragmented by sonication, then immunoprecipitated according to the method of the invention.

Following formation of a CO:target complex in step b, non-specific complexes are removed by washing. In one embodiment, the complexes are washed with a low sodium wash solution. In one embodiment, a low sodium wash solution comprises 10 mM NaCl, 10 mM HEPES pH 7.7, 2 mM EDTA, 1 mM EGTA, and 0.2% SDS. In one embodiment, the complexes are washed sequentially with 8 M Urea, 6 M Guanidinium chloride and 35% Formamide wash solution. In one embodiment, the wash is performed at a temperature of at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., at least 50° C., at least 51° C., at least 52° C., or greater than 52° C. In one embodiment, the complexes are washed with 10 mM NaCl, 10 mM HEPES pH 7.7, 2 mM EDTA, 1 mM EGTA, and 0.2% SDS at 50° C. to remove non-specific complexes and improve the signal-to-noise ratio.

Biological Sample

The biological sample can be any sample from which a nucleic acid molecule can be obtained. In one embodiment, the nucleic acid molecule represents a sample of genomic DNA isolated from a cell or a subject. In one embodiment, the nucleic acid molecule represents an RNA molecule isolated from a cell or a subject. The biological sample(s) can be prepared using methodologies well known in the art such as by obtaining a specimen from an individual and, if necessary, disrupting any cells contained thereby to release genomic nucleic acids.

Biological samples which can be tested by the methods of the present invention described herein include human cells, tissues and body fluids such as whole blood, serum, plasma, cerebrospinal fluid, sputum, bronchial washing, bronchial aspirates, urine, lymph fluids and various external secretions of the respiratory, intestinal and genitourinary tracts, tears, saliva, milk, white blood cells, myelomas, buccal cells, cervicovaginal cells, epithelial cells from urine, fetal cells, or any cells present in tissue obtained by biopsy and the like; biological fluids such as cell culture supernatants; tissue specimens which may be fixed; and cell specimens which may be fixed.

This nucleic acid molecule may be obtained from any cell source, tissue source, or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, semen and tissue exudates at a site of infection or inflammation. Nucleic acid molecules are extracted from the cell source, tissue source, or body fluid using any of the numerous methods that are standard in the art. It will be understood that the particular method used to extract the nucleic acid molecule will depend on the nature of the nucleic acid molecule and the nature of the source.

In one embodiment, multiple samples are amplified individually using the method of the invention and pooled together prior to sequencing using a Next Gen Sequencing platform. In one embodiment, multiple samples may be from the same type of biological sample (e.g. all FFPE samples). In one embodiment, multiple samples may be from different types of biological samples.

Nucleic Acid Samples And Preparation

As contemplated herein, the present invention may be used in the analysis of any nucleic acid sample for which next generation sequencing may be applied. For example, the nucleic acid can be from a cultured cell or cells or a patient cell or tissue or bodily fluid sample. The nucleic acid may be isolated using methods generally known to those of skill in the art, including, methods which preserve protein-DNA insteractions and methods which are readily immobilized or immunoprecipitated.

The nucleic acid may be prepared (e.g., library preparation) for massively parallel sequencing in any manner as would be understood by those having ordinary skill in the art. While there are many variations of library preparation, the purpose is to construct nucleic acid fragments of a suitable size for a sequencing instrument and to modify the ends of the sample nucleic acid to work with the chemistry of a selected sequencing process. Depending on application, nucleic acid fragments may be generated having a length of about 25 to about 1000 bases. It should be appreciated that the present invention can accommodate any nucleic acid fragment size range that can be read by a sequencer. This can be achieved by selecting primers such that the resulting PCR product is within the desired range specific for the sequencer and sequencing method desired. For example, in various embodiments a desired PCR fragment size, including barcode and adaptor regions is about 100, 150, 200, 250, 300, 350, 400, 450 or about 500 bp. Both the 5' and 3' ends of the PCR products comprise nucleic acid adapters. In various embodiments, these adapters have multiple roles, such as allowing attachment of the specimen strands to a substrate (bead or flow cell) and having a nucleic acid sequence that can be used to initiate the sequencing reaction through hybridization to a sequencing primer. Further, in some embodiments, the PCR products also contain unique sequences (bar-coding) that allow for identification of individual samples in a multiplexed run. The key component of this attachment process is that each individual PCR product is attached to a bead or location on a slide or flow cell. This single PCR fragment can then be further amplified to generate hundreds of identical copies of itself in a clustered region on the bead, flow cell or slide location. These clusters of identical DNA form the product that is sequenced by any one of several next generation sequencing technologies.

The samples can be sequenced using any massively parallel sequencing platform. Non-limiting examples of sequencers include Illumina/Solexa GAII, AB SOLiD system, Ion Torrent PGM, Ion Proton, Illumina MiSeq, Illumina HiSeq 2000 or 2500 and the like.

PCR Primers

In various embodiments, the assay comprises a combination of at least one forward and at least one reverse PCR primer. In some embodiments, a forward primer of the invention comprises at least a region complementary to a sequence of an adaptor molecule that has been ligated to a target nucleic acid molecule. In some embodiments, a reverse primer of the invention comprises at least one of a region complementary to a sequence of an adaptor molecule that has been ligated to a target nucleic acid molecule, a sample barcode region, and a sequencing adaptor region. The sequencing adaptor region allows for hybridization to a NGS-based sequencing platform, such as a bead or flow cell.

In one embodiment, a sequencing adaptor region comprises a sequence specific for use in an Ion Torrent sequencing system. In one embodiment, a sequencing adaptor region comprises a sequence specific for use in an Illumina sequencing system.

Methods of Identification of Binding Sites

As contemplated herein, the present invention includes methods of analyzing Next Gen Sequencing data. Generally, sequence reads are aligned, or mapped, to a reference sequence using, for example, available commercial software or open source freeware (e.g., nucleotide and quality data input, mapped reads output). This may include preparation of read data for processing using format conversion tools and optional quality and artifact removal filters before passing the read data to an alignment tool. Next, variants are called (e.g., summarized data input, variant calls output) and interpreted (e.g., variant calls input, genotype information output).

Standard approaches to mapping and analysis of this type of massively parallel sequence data are applicable to the invention described herein. In some embodiments, an analytical pipeline may detect the binding sites of a protein of interest, as outlined in the method below. First, raw read data, which may include sequence and quality information from the sequencing hardware, is received and entered into the system. The data is optionally prefiltered, for example, one read at a time or in parallel, to remove data that is too low in quality, typically by end trimming or rejection. For a multiplexed sequencing reaction, the raw reads are sorted according to the barcode region to group reads from each individual sample. The reads are then trimmed to remove barcode and adaptor sequences.

The remaining data is then aligned using a set of reference sequences. Read data can be mapped to reference sequences using any mapping software, and using appropriate alignment and sensitivity settings suitable for the goal of the project. Mapped reads may optionally be postfiltered to remove low quality or uncertain mappings. The total numbers of aligned reads can be determined using any appropriate method including, but not limited to, SAMtools, a PERL script, a PYTHON script, and a sequencing analysis pipeline.

In various embodiments, at least 1000, at least 2000, at least 3000, at least 4000, at least 5000, at least 10,000, at least 50,000, at least 100,000, at least 500,000 or more than 500,000 sequencing reads are determined to be 'high quality' after passing quality filters. In one embodiment, 'high quality' sequencing reads are aligned to one or more reference sequences.

Kits

In one embodiment, the invention provides a kit for use in the thCHART method of the invention. In one embodiment, the kit comprises one or more of: (a) at least one CO; (b) at least one PO; and (c) at least one EO.

In one embodiment, the kit comprises one or more reagents to wash the CO:target complexes including, but not limited to, low sodium wash solution (10 mM NaCl, 10 mM HEPES pH 7.7, 2 mM EDTA, 1 mM EGTA, 0.2% SDS), 8 M Urea, 6 M Guanidinium chloride and 35% Formamide.

Any kit of the invention may also include suitable instructional material, storage containers, e.g., ampules, vials, tubes, etc., for each reagent disclosed herein, an reagents used as controls, e.g., a positive control nucleic acid sequence or positive control antibody). The reagents may be present in the kits in any convenient form, such as, e.g., in a solution or in a powder form. The kits may further include a packaging container, optionally having one or more partitions for housing the various reagents.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Harnessing LNA and Toehold-Mediated Strand Exchange to Reveal the Chromatin Spreading Pattern of an Endogenous LNCRNA Here a new hybridization capture method is described called ToeHold CHART (thCHART), which uses toehold-mediated strand exchange reaction to specifically hybridize LNA-containing antisense oligonucleotide to intended RNA target (FIG. 1A). thCHART has been developed as a powerful and highly specific hybridization capture method for enrichment of endogenous RNAs and their associated chromatin loci. The core of this method is to specifically hybridize RNA target to LNA modified antisense oligonucleotide at ambient temperature thanks to its dual-toehold design. This combined with improved rinse and elution conditions provides dramatically superior signal-to-noise ratios.

thCHART is highly reproducible and can produce high quality data with capture oligonucleotides of different design, as well as easily adaptable to RNA targets of various lengths or tissue origin. thCHART was used to investigate chromatin localization of 17 kbp long mouse Xist lncRNA using a single antisense oligonucleotide. Previous versions of hybridization capture methods used pools of oligonucleotides to enrich target RNA, but the results indicated that using smaller number of oligonucleotides can have positive effect on specificity of RNA enrichment (Quinn et al., 2014, Nature biotechnology 32(9): 933-940). The experiments presented show that proper placement can mitigate the necessity of many oligonucleotides and even a single oligonucleotide can be sufficient to investigate RNA-chromatin association.

The high signal-to-noise ratio is essential for accurate identification of chromatin association especially for cases where signal enrichment is very low. Thanks to the improvement in signal-to-noise ratio in thCHART data, roX2 ncRNA and MSL complex localization was detected with high confidence and quality at loci that were previously avoiding detection with current methods. A comparison of the roX2 thCHART with published RNA-seq and modENCODE ChIP-seq data revealed that the identified loci hold hallmarks of active transcription of the underlying genes. Since a function of the MSL complex is to upregulate expression of the active X-linked genes, this correlation confirms the sensitivity and the specificity of thCHART. Further, low amounts of RNA and DNA material were sufficient to create NGS libraries for roX2 and Xist RNAs using the thCHART method.

Previous studies observed differences of MSL localization in distinct tissues and stages of Drosopihla development, but the dynamics of changes in MSL localization within a given cell type or a tissue was not determined. Here it is demonstrated that chromatin localization of MSL complex dramatically and rapidly (within 1 hour) changes during heat-shock stress. Heat-shock is known to change gene transcription, which in turn can affect MSL complex association. Yet, induction or inhibition of transcription alone does not affect MSL localization, which suggest that more active processes must take place during heat-shock that assist MSL removal. Why MSL complex dissociates from chromatin upon heat-shock is not clear. However, the removal of MSL complex could result in lower expression of the chromosome X genes and therefore decrease a chance of creating new misfolded proteins, which gives the cell a better chance to minimize the damage caused by the stress conditions. Further investigating will be needed to clarify whether other stress conditions such as hyperosmosis or acid shock have the same effect on MSL complex localization, or whether other chromatin modifying complexes that deposit active chromatin marks (e.g. MLL1) are similarly affected as well.

Based on the experiments present, thCHART allows for precise and sensitive detection of ncRNA interaction with chromatin. thCHART is highly reproducible and adaptable to various lncRNAs. In addition, it allowed for the detection of MSL complex localization at distal sites, which avoided previous detection due to high background levels in the current hybridization capture methods. thCHART was utilized to investigate the dynamics of MSL complex distribution and it was found that after heat-shock, the MSL localization undergoes a rapid and dramatic change that can't be explained by change in transcription levels. thCHART therefore allows for investigation of dynamic processes that accompany ncRNA complexes spreading and localization to chromatin.

The Materials and Methods used are now described.

Oligonucleotide Design

To design capture oligonucleotides for thCHART, the previously published 'NAB Lab probe designer' (Wu et al., 2015, Nat Methods, 12(12):1191-1196) MatLab script was modified to accommodate the option of using RNA protecting oligonucleotides. The sequence of the target ncRNA, previously validated as accessible for capture oligonucleotide hybridization, was extended by two nucleotides on each side and submitted as input for designing script along with following parameters: 30° C. temperature, 0.817M Na+ concentration, 75% desired yield. Oligonucleotides design was accepted if expected yield was close to desired yield and second (non-homologous) toehold length was at least 4 nucleotides. Capture oligonucleotide (CO) was modified so that every second nucleotide of its central region is LNA nucleotide and the 3' end oligonucleotide was attached to biotin-TEG modification and ordered from Exiqon. Protection oligonucleotide was synthetized as RNA (IDT). Sequence of CO was turned into reverse complement to create elution oligonucleotide (EO) ordered as 2'O methyl modified RNA (IDT).

Oligonucleotide Annealing

On the day of thCHART experiment, the CO and PO were annealed in 1:1.02 ratio to the create CO:PO pair. CO and PO were added to the annealing buffer (100 mM NaCl, 20 mM Tris-HCl pH 7.4 final concentration) and annealed on PCR cycler by denaturing the mix at 95° C. for 2 minutes and then cooling at rate of 2° C./minute until temperature reached 20° C. This created ~10 μM final concentration of CO:PO hybrids.

thCHART

Drosophila S2 cells were grown in Schneider medium (Lonza) supplemented with 10% heat-inactivated FBS and penicillin/streptomycin at 27° C. Total of 300×10⁶ cells were harvested by centrifugation at 500×g for 5 minutes and washed 2 times with PBS. Washed cells were crosslinked for 10 minutes at room temperature in 1% methanol-free formaldehyde (Thermo) solution in PBS supplemented with 0.1% Tween-20. The reaction was stopped by adding Glycine to 12.5 mM (final concentration) and centrifuged at 500×g for 5 minutes at 4° C. After washing the cells 2× with cold PBS, the pellets were either stored at −80° C. or used processed further. The pellet was resuspended in cold Sucrose buffer and the nuclei were isolated by douncing 20× with tight pestle and incubation 10 minutes on ice. Cell suspension was then carefully overlaid over equal volume of Glycerol buffer and centrifuged at 1000×g for 5 minutes at 4° C. Pellet was resuspended Sucrose buffer and nuclei were isolated one more time. Nuclei were then resuspended in PBS+0.1% Tween-20 and crosslinked second time for 45 minutes at room temperature in 3% methanol-free formaldehyde (Thermo) solution in PBS supplemented with 0.1% Tween-20. To stop the reaction glycine solution was added to 100 mM (final concentration) and centrifuging at 1000×g for 5 minutes at 4° C. The crosslinked nuclei were washed 2× with cold PBS+0.1% Tween-20 suspending the pellet in Dounce homogenizer. Washed nuclei were equilibrated by incubating in 1 ml cold Sonication buffer for 10 minutes on ice. After centrifugation, the pellet was finally resuspended in 0.9 ml of cold Sonication buffer contacting 5 mM DTT, 0.9 μl Superase-In (Thermo Fisher Scientific) and protease inhibitors (Roche). To shear the genomic DNA, 130 μl of nuclei were transferred to Covaris microTube and sonified on 5220 instrument (Covaris) using following settings: 200 W peak incident power, 20% duty factor, 200 bursts per cycle for 1 minute. The cell lyzate was cleared by centrifugation at 20,000×g for 20 minutes at 4° C. and 150 μl of the supernatant was transferred to DNA LoBind tube (Eppendorf) and left equilibrate to ambient temperature for 10 min. The extract was mixed with 75 μl of Denaturant buffer and incubated for 1 minute at room temperature. Extract was further diluted with 225 μl of 2× Hybridization buffer and supplemented with DTT (1 mM final), protease inhibitors (Roche) and 2.25 μl Superase-In (Thermo Fisher Scientific) and incubated at room temperature for 8 minutes. To diluted thCHART extract, 6 μl of 10 μM CO:PO hybrids (133 nM final) were added and incubated overnight at room temperature.

The next day, hybridized extract was pre-cleared by centrifuging at 20,000×g for 20 minutes at 22° C. and the supernatant was transferred to fresh DNA LoBind tube containing 60 μl of Dynabeads MyOne streptavidin C1 magnetic beads (Thermo Fisher Scientific) and captured for 2 hours at room temperature. Beads were then washed 5× with ePICh100 buffer for 5 minutes, transferred to fresh DNA LoBind tubes and washed 2× with ePICh100 buffer. Beads were then further washed for 5 minutes with 1× with ePICh30 buffer at 42° C., 1× with ePICh10 buffer at 42° C. and 1× with ePICh10 buffer at 50° C. In order to elute the captured complexes, the beads were resuspended in 87 μl Elution buffer supplemented with 1 μl of 1 M DTT, 5 μl Superase-In (Thermo Fisher Scientific) and 7.5 μl of 100 μM EO, and incubated for 1.5 hours at room temperature. The eluted RNA-complexes were reverse-crosslinked by adding 10 μl of 10% SDS and 5 μl of Proteinase K (Thermo Fisher Scientific) and incubating 1 hour at 55° C. followed by incubation at 65° C. for 1.5 hours.

Eluted material was used to either isolate RNA using RNAeasy kit (Quiagen) or DNA using PCR purification kit (Quiagen) and analyzed by qPCR or used to construct sequencing libraries.

The Results of the Experiments are now described.

Designing toehold CHART (thCHART)

Detecting chromatin localization of lncRNA complexes is notoriously difficult, because these interactions are typically weak. To stabilize these contacts, hybridization capture methods use strong but specific crosslinking conditions (e.g. 3% formaldehyde). The crosslinked chromatin is mechanically sheared and under denaturing conditions a pool of biotinylated antisense capture oligonucleotides (COs) are hybridized to lncRNA target. However, COs can also spuriously hybridize to RNAs of similar sequence or even correctly hybridized lncRNA target can provide its single stranded regions for hybridization to other unintended molecules. All this leads to off-target recovery and decrease in signal-to-noise ratio of the resulting data (Simon et al., 2016, Biochim Biophys Acta, 1859(1): 121-127; Machyna and Simon, 2017, Brief Funct Genomics, 17(2):96-103).

Without being bound by theory, it was hypothesized that increasing the hybridization energy of CO by incorporating locked nucleic acid (LNA) nucleosides would strengthen the CO-RNA interaction and allow us to use more denaturing, stringent wash conditions. Under these conditions, relatively weaker off-target interactions would be removed, while the native interactions would be preserved through formaldehyde crosslink and LNA CO contacts. Similar strategies were previously used with only a limited success [RAP, ChIRP, Hentze], (Simon et al., 2011, Proc Natl Acad Sci USA 108(51): 20497-20502; Castello et al., 2013, Nature protocols 8(3): 491-500; Engreitz et al., 2013, Science 341(6147): 1237973; Rogell et al., 2017, RNA, 23(8): 1290-1302) as the increase in energy (affinity) of hybridization is met with proportional decrease in specificity (Demidov and Frank-Kamenetskii., 2004, Trends in biochemical sciences 29(2): 62-71; Murugan, 2005, Biophysical chemistry 116(2): 105-109). This is because of extremely negative AG of the hybridization reaction, where the excess of the energy produced during hybridization overcomes the small energy penalties imposed by base pair mismatches (Demidov and Frank-Kamenetskii., 2004, Trends in biochemical sciences 29(2): 62-71). The hybridization specificity could be restored by increasing temperature during the hybridization, but such conditions are not always compatible with RNA integrity (Murugan, 2005, Biophysical chemistry 116(2): 105-109). Therefore, to enable specific hybridization of LNA containing COs under room temperature conditions, a previously described dual-toehold oligonucleotide design (Wu et al., 2015, Nat Methods, 12(12):1191-1196) was adapted.

Figure 1B:
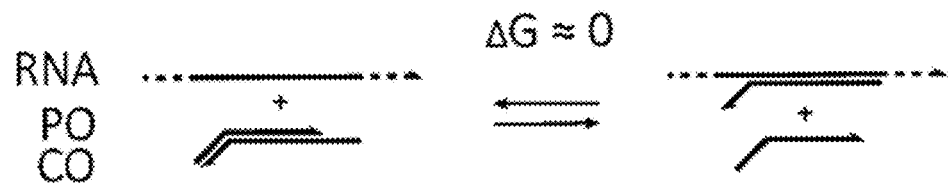
Figure 1B:
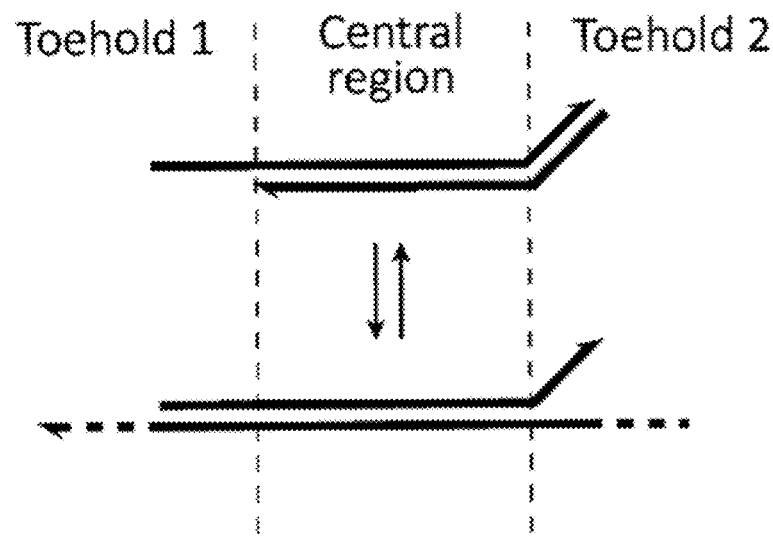

In dual-toehold design, COs are pre-annealed to protecting oligonucleotide (PO) and hybridize to target RNA through toehold-mediated strand exchange reaction. At the end of the reaction, the PO strand is released and acts as a competitor to target RNA, making the reaction reversible (FIG. 1B). By accurately designing of CO-PO and CO-RNA hybridization energies one can achieve less negative AG, which has positive effect on specificity, while maintain good hybridization yields. The prerequisites for correct toehold probe design was previously formalized (Wu et al., 2015, Nat Methods, 12(12):1191-1196) and require information about free energies of both toeholds and the central region of the CO (FIG. 1B). However, the current knowledge of LNA hybridization energies is incomplete thus posing an obstacle in accurate CO design. To overcome these limitations, two modifications were introduced: 1) PO strand being made of RNA nucleotides and 2) limiting the use of LNA nucleotides to the central region of the CO. Together these modifications result in central region of CO to have the same hybridization energy when hybridizing to RNA PO or RNA target, thus dramatically simplifying the designing process (FIG. 1B).

Capturing RNA In Vitro

Figure 1C:
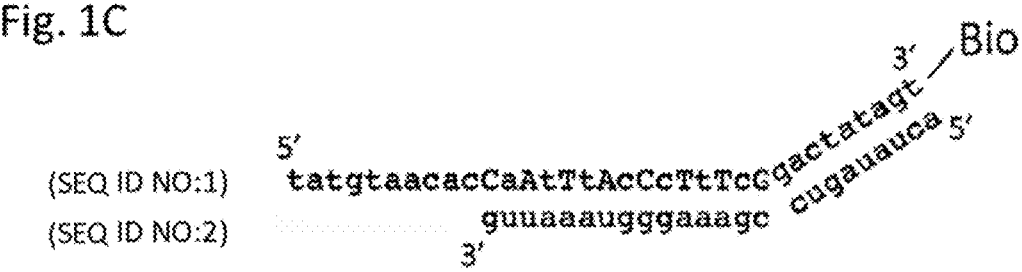
Figure 1D:
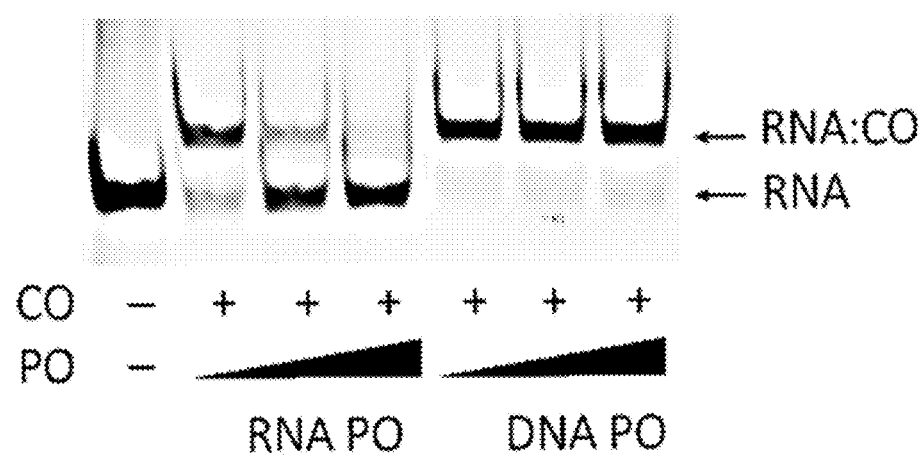

This simplified strategy was used to design a CO:PO pair against Drosophila roX2 lncRNA. The designed 34 nt CO consists of two DNA toeholds and central region where every second position holds LNA nucleotide leading to increase of melting temperature from 54 to 83° C. The CO is pre-hybridized to RNA PO and contains biotin moiety attached to its 3' end through 15 atom linker (FIG. 1C). To verify the accuracy of the design strategy, the tunability of the strand exchange reaction was tested using a gel shift assay. Fluorescently labelled fragment of roX2 RNA was left to hybridize with CO in the presence of increasing amounts of PO and analyzed on native gel (FIG. 1D). At 1:1 ratio (CO:PO), the LNA CO readily hybridized to RNA target, but by increasing the concentration of free PO (1:10) in the reaction, the hybridization yield dropped from 75% to 16%. In contrast, providing excess of DNA version of the PO did not lead to any significant change in hybridization yield. These results show that dual-toehold design with RNA PO can hybridize LNA CO to RNA at room temperature by successfully shifting reaction AG to less negative values as demonstrated by the tunability of the reaction.

Encouraged by these results, improved wash conditions were sought that would remove hybridization induced off-targets while preserving the most of the correctly hybridized target RNA. A simple wash assay was developed where CO hybridized to fluorescently tagged RNA is immobilized to streptavidin beads, subjected to series of washes and the RNA remaining on the beads is quantified by measuring fluorescence. To simulate off-target hybridization, a DNA version of CO was used and conditions that would results in the highest loss of RNA retention compared to LNA CO were identified. Several wash conditions were screened and it was determined that the highest difference of RNA retention is observed in low salt (10 mM NaCl) and increased temperature (50° C.) (FIG. 1E), indicating that LNA COs can improve off-target removal.

Figure 1E:
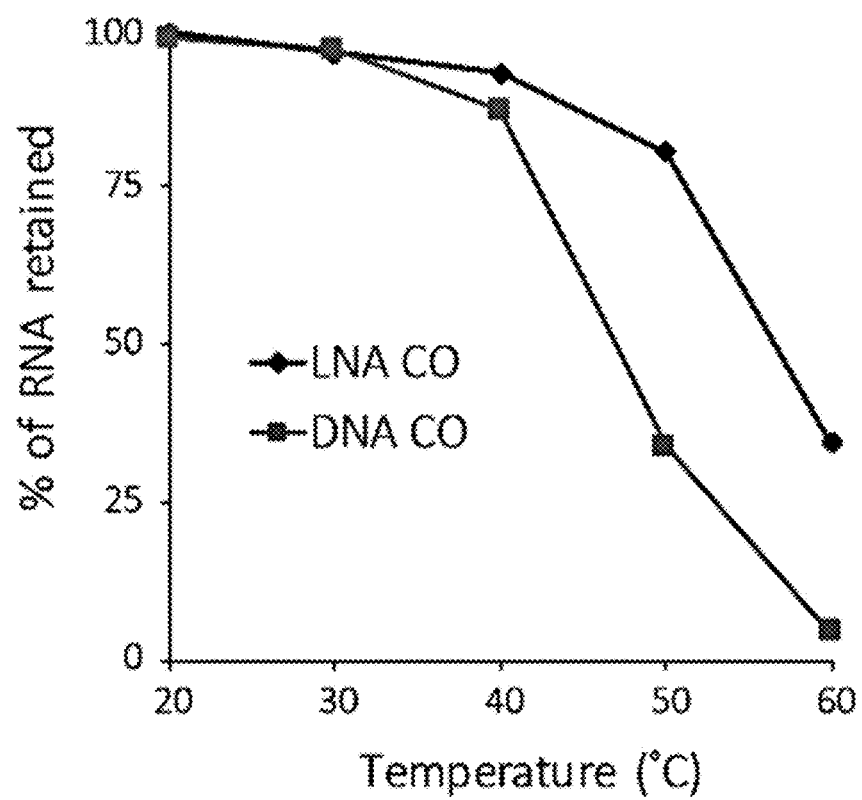
Figure 1F:
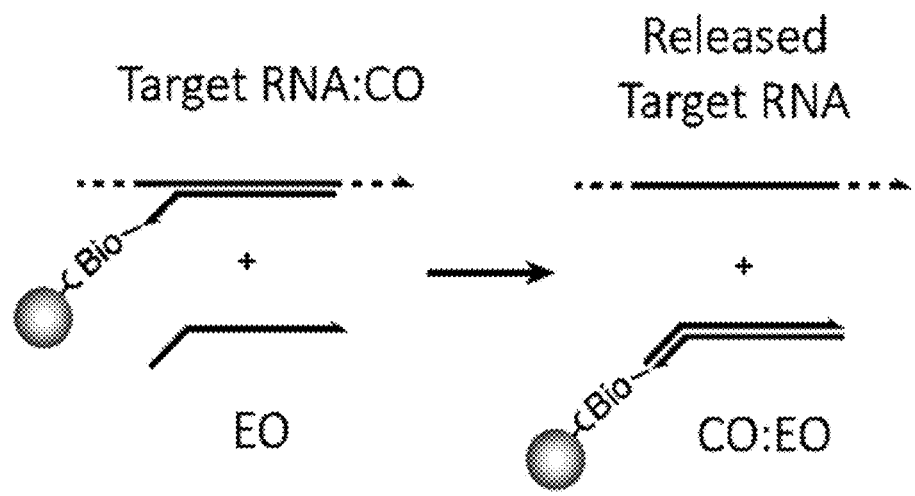
Figure 1G:
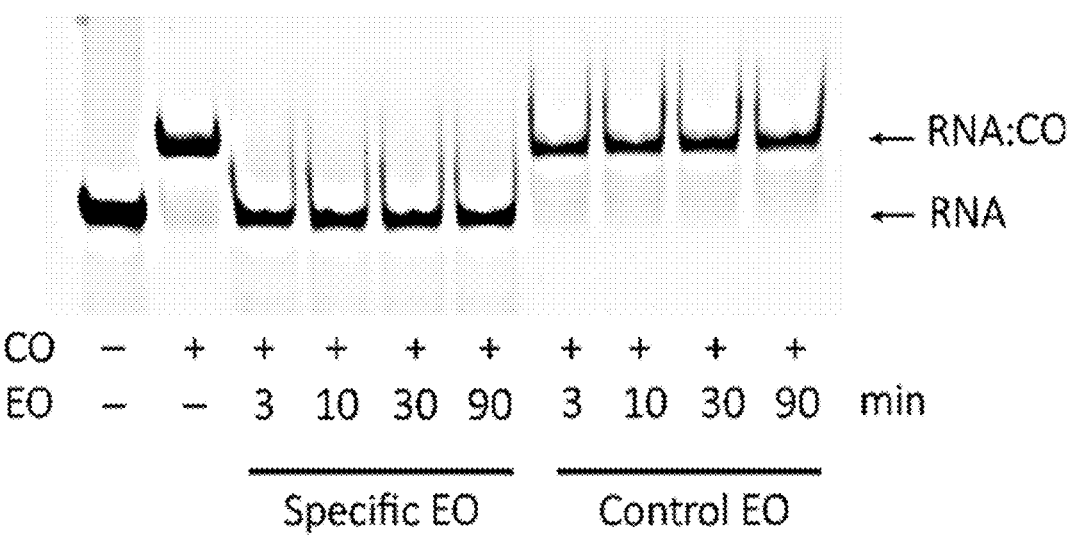

Another step that influences contamination with background signal is the elution step. Using unspecific elution such as proteinase K or RNase A digest releases target RNA as well as unspecific molecules from the beads. Previously, it was reported that using more specific elution strategies such as RNase H digestion can reduce background in hybridization capture data (Simon et al., 2011, Proc Natl Acad Sci USA, 108:20497-20502). However, LNA nucleotides protect RNA from RNase H cleavage, which make LNA COs unusable for RNase H elution. Therefore, 'toehold 2' region of CO was utilized and an elution strategy was devised where antisense elution oligonucleotide (EO) hybridizes to CO via strand exchange reaction and displaces RNA target (FIG. 1F). The efficiency of this system was tested by incubating RNA-CO hybrids with 50 molar excess of 2' O-Methyl EO. The results show that the elution is rapid and highly specific as 100% of RNA is displaced after a 3 minute incubation, but control EO does not displace RNA even after a 1.5 hour incubation (FIG. 1G). This data demonstrates that elution strategy using EO can be used to efficiently recover DNA, RNA and potentially protein molecules simultaneously without losing any of the interacting molecules.

thCHART improves signal-to-noise of roX2 lncRNA pull-down

After establishing the in vitro properties of thCHART, its properties were validated on enrichment of endogenously expressed lncRNA. RoX2 is 600 nt lncRNA, which as part of the male sex lethal (MSL) complex plays role in establishment and maintenance of dosage compensation in Drosophila. The localization of MSL complex and roX2 lncRNA was previously studied using hybridization capture methods. It was determined that roX2 localizes to defined regions on male chromosome X called chromatin entry sites from where it spreads to neighboring active genes.

To perform roX2 enrichment, a male Drosophila S2 cell line was used that stably expresses roX2 RNA and has a functional dosage compensation. First the difference in roX2 enrichment was compared when LNA-containing CO is hybridized as single stranded probe or through toehold-mediated strand exchange. The qPCR results of enriched RNAs showed that single stranded LNA CO alone co-purifies non-intended RNA off-targets, which results in poor roX2 enrichment ratio. In contrast, using the toehold version of LNA CO led to dramatic reduction in off-target RNA recovery, which improved enrichment ratios to similar levels that are achieved with of DNA CO (FIG. 2a). This confirms the expectations that hybridizing high affinity probes at room temperature conditions leads to high rate of off-target hybridization. Further, the results demonstrate that the specificity of the hybridization in such cases can be restored by using dual-toehold design with RNA PO.

To test if using stringent wash can indeed reduce amount of off-target RNA recovery, roX2 RNA enrichment was repeated using LNA CO with dual-toehold design followed by washes with reduced salt concentration at 50° C. (FIG. 1E). Applying stringent wash conditions significantly improved roX2 enrichment ratio compared to 'mild wash' conditions previously described for CHART (FIG. 2B). Interestingly, stringent wash conditions also improved enrichment ratio for DNA CO, although to a lesser extent.

Figure 3A:
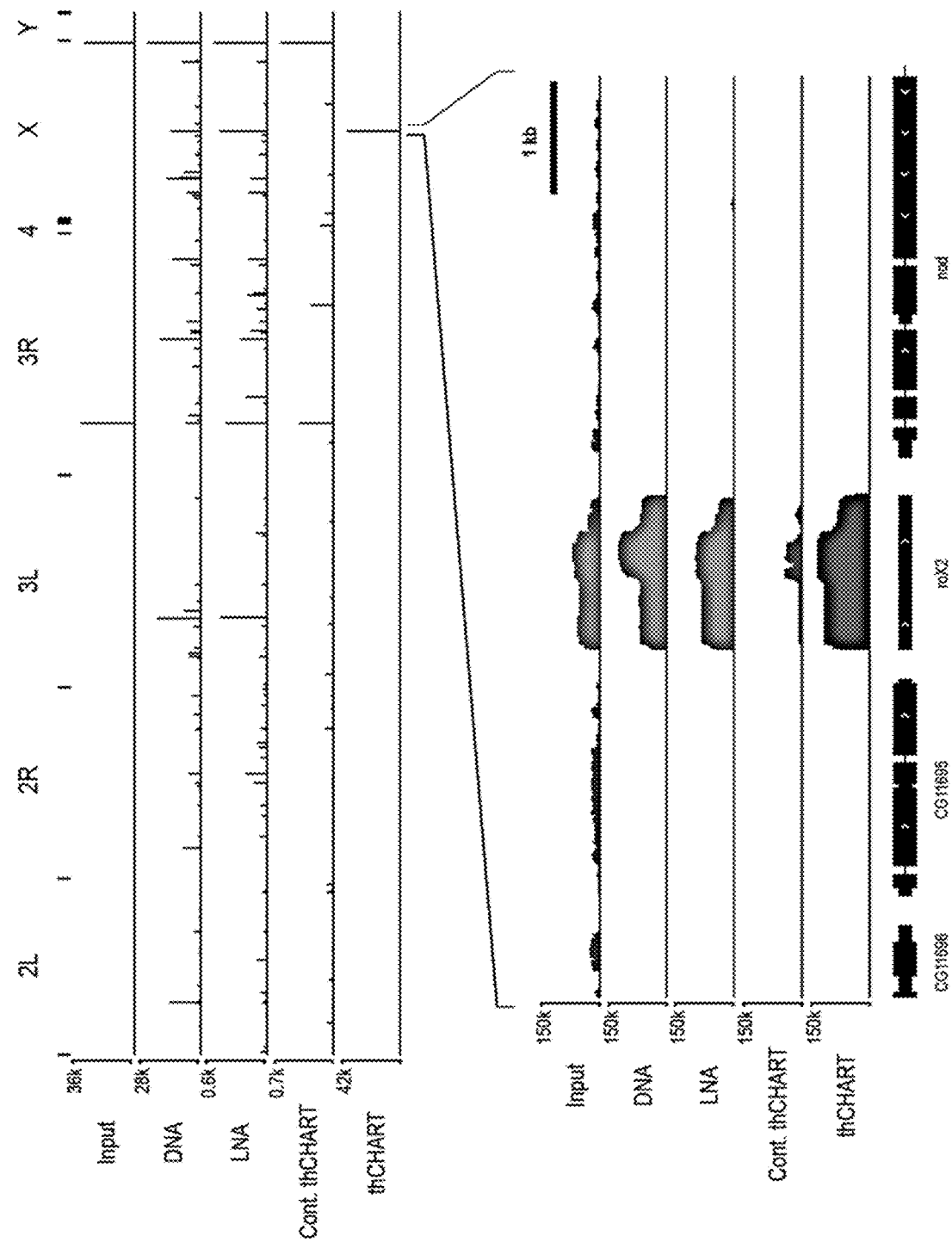
FIG. 3A through FIG. 3C depict exemplary experimental results demonstrating that thCHART profile highlighted roX2 as the main enriched RNA.
Figure 3C:
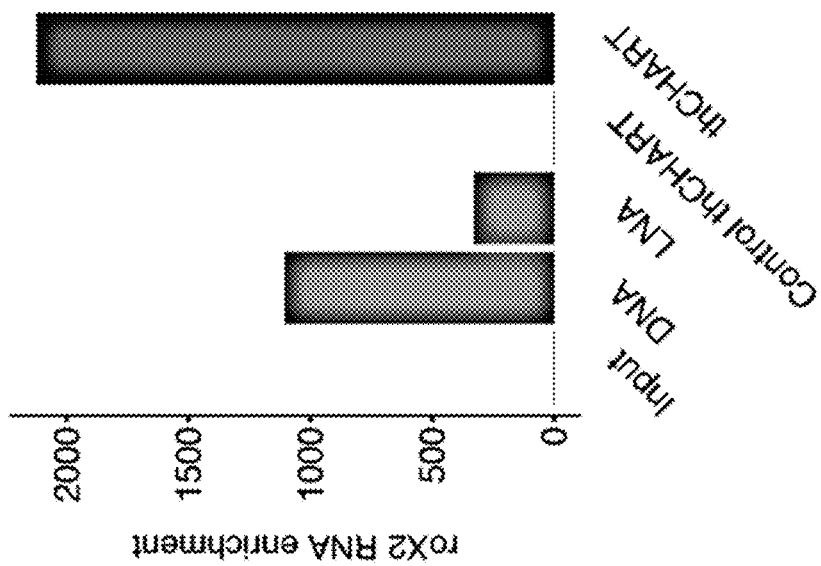
Figure 3B:
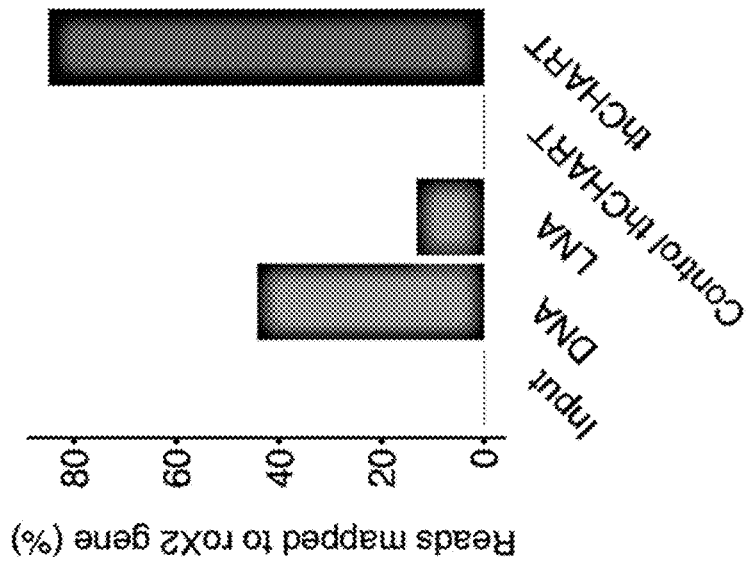

To further test the full potential of thCHART, roX2 pull-down was performed with stringent wash conditions followed by elution using EO. Including EO lead to a further increase in the roX2 enrichment ratio, which improved more than 250-fold over the original CHART protocol (FIG. 2C). This improvement was also apparent from transcriptome-wide data. High-throughput sequencing of the eluted RNA revealed that RNase H CHART co-purifies many other RNA species throughout the Drosophila genome, while thCHART profile highlighted roX2 as the main enriched RNA (FIG. 3A). This resulted in 85% of the reads aligned to transcriptome from the thCHART experiment were originating from roX2 locus leading to 2000-fold enrichment over input total RNA-seq (FIG. 3B and FIG. 3C). Interestingly, performing thCHART where LNA CO was hybridized as single stranded probe and not through strand-exchange reaction led to dramatic loss of specificity, which further demonstrates the usefulness of dual-toehold design in maintain hybridization specificity for high-affinity probes. No roX2 enrichment was observed in thCHART with control LNA CO.

Significant improvement of signal-to-noise ratio was also observed in enrichment of roX2 associated chromatin loci. The qPCR analysis of co-purified DNA showed that thCHART specifically detected roX2 lncRNA interaction with roX2 and chromatin entry site loci, while recovery of autosomal region was dramatically reduced compared to CHART protocol (FIG. 2D). These results demonstrate that thCHART approach can be successfully used to enrich endogenous RNA and associated chromatin with high specificity.

thCHART Reproducibly Reveals Genome-Wide lncRNA Localization

Figure 4A:
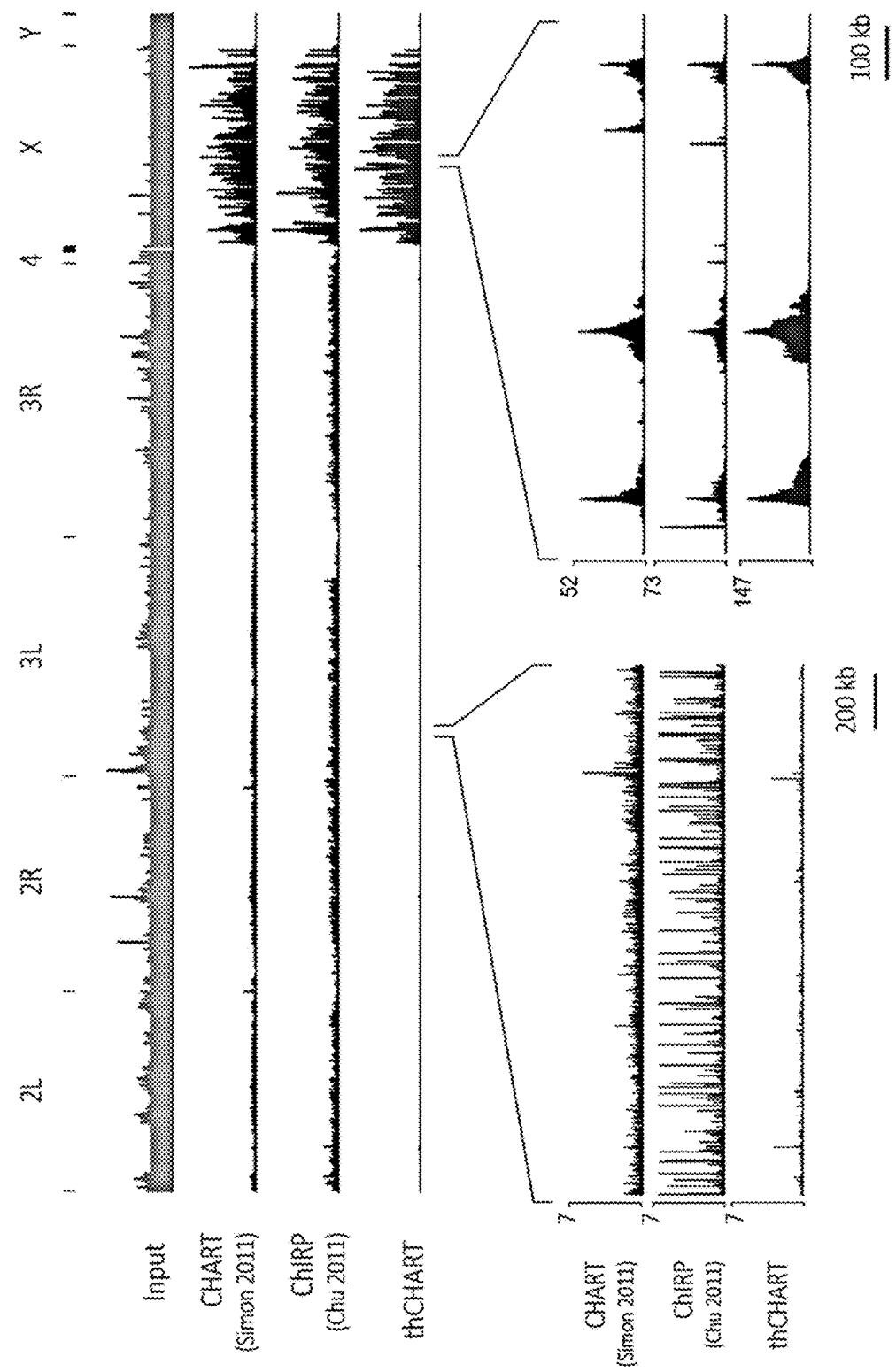
FIG. 4A through FIG. 4D depict exemplary experimental results demonstrating thCHART has greatly improved signal specificity.
Figure 4D:
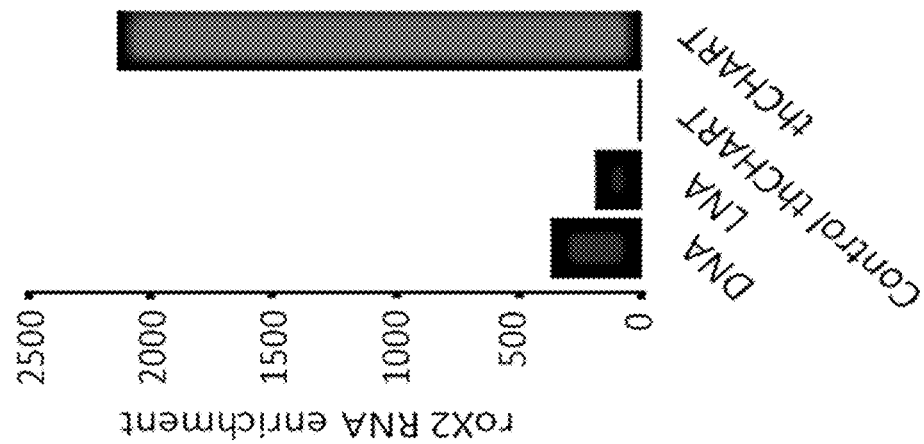
Figure 4C:
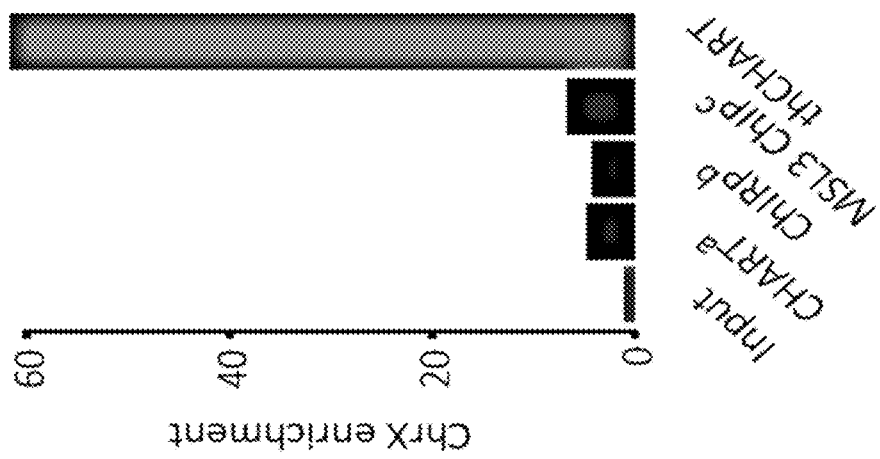

The observed improvement in enrichment of roX2 associated chromatin loci prompted us to investigate the binding profile genome-wide. roX2, as part of MSL complex, is known to associate with X chromosome while being absent from Y and autosomal chromosomes. Previous roX2 genome-wide studies used either a pool of antisense oligonucleotides spanning the full RNA length (ChIRP) or mixture of three capture oligonucleotides targeting different regions of the RNA (CHART) in order to detect its chromatin localization. Since, some reports suggest that smaller number of oligonucleotides can lead to improvement in signal quality (Quinn et al., 2014, Nature biotechnology 32(9): 933-940) experiments were performed to test if using a well-designed single oligonucleotide would help to improve background removal in thCHART. After aligning sequencing reads to fly genome, the vast majority of thCHART signal was originating from chromosome X. Closer examination of the X chromosomal regions revealed that roX2 thCHART signal closely recapitulates peaky profile described in previous CHART and ChIRP studies of roX2 (FIG. 4A). However, the CHART and ChIRP profiles also contain noticeable amount of signal on the autosomal chromosomes (FIG. 4A). The intensity and localization of the autosomal signal is highly variable between repeated experiments, which is highly indicative of background contamination. This is supported by previous FISH experiments that detect roX RNAs only on chromosome X. In contrast, thCHART data profile showed dramatically reduced autosomal signal demonstrating efficient background removal. Similar reduction in background was also observed in X chromosomal regions between bona fide roX2 peaks (FIG. 4A).

Figure 4B:
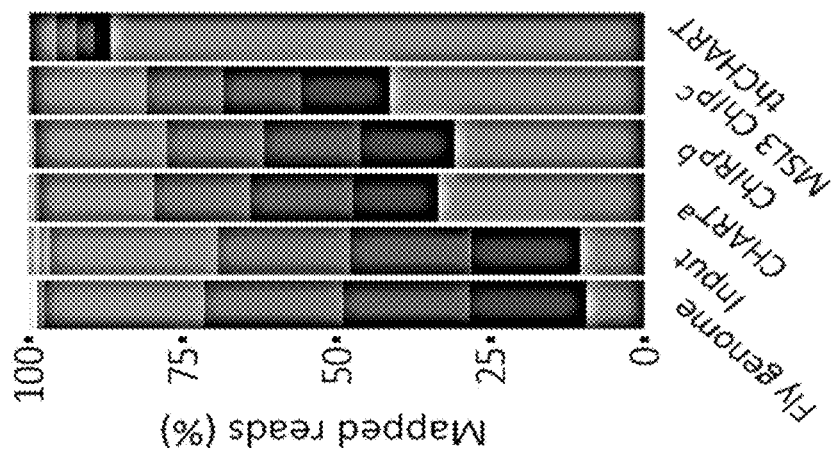

This reduction in background is even more apparent when sequencing reads were counted that were aligned to individual chromosomes. In both previously published roX2 CHART and ChIRP data, the majority of the uniquely mapped reads (67% and 69% respectively) originated from autosomes or mitochondrial genome (FIG. 4B). However, in thCHART the total amount of non-chromosome X reads condensed to merely 13%, which lead to 13-fold improvement of chromosome X enrichment over the autosomes (FIG. 4B). For comparison, MSL3 ChIP-seq performed by tandem affinity purification (TAP) was re-analyzed. TAP style of enrichment is generally viewed as very specific, because of two consecutive purification steps that allow for extended background removal. Nevertheless, MSL3 ChIP contained similar levels of autosomal reads as CHART and ChIRP datasets, causing a poor chromosome X sequences enrichment (FIG. 4A and FIG. 4B). This suggests that thCHART protocol can be used to enrich for RNA-associated chromatin region with extreme specificity, which has a potential to surpass other RNA and protein-centric methods.

The results also demonstrate that a single well designed antisense oligonucleotide can be sufficient to capture all RNA-chromatin interaction sites. However, depending on which sequences of the RNA are targeted by oligonucleotides, it can result in different distribution of the signal. For example, comparing 'odd' and 'even' ChIRP datasets—prepared with two non-overlapping pools of oligonucleotides—revealed large amount of high-intensity signal that is anti-correlated between datasets (FIG. 5D). To examine whether thCHART can eliminate such sequence-dependent variability, a second thCHART oligonucleotide was designed targeting roX2 at a different location (CO2) and the enrichment was repeated with either oligonucleotide. At the whole genome level, CO2 specifically enriched chromosome X regions, while autosomal regions were depleted compared to CHART and ChIRP (FIG. 5A). Analysis of the reads distribution showed that CO2 has reduced number of reads originating from autosomes and also improved chromosome X enrichment although to a lesser extent than CO1 (FIG. 5B and FIG. 5C). Direct comparison of signal distribution on chromosome X revealed that both CO1 and CO2 data is highly correlated (FIG. 5E) suggesting that thCHART does not suffer from sequence-dependent signal variability.

To further test the thCHART versatility, experiments were designed to attempt to enrich chromatin regions associated with very long RNA using a single CO. While roX2 with its 600 nt length represents a relatively easy RNA target, the majority of cellar RNAs are more than a magnitude longer such as 17 kb long Xist lncRNA. Xist lncRNA plays important role in initiating and maintaining of chromosome X inactivation in mammals. During the process of inactivation, Xist is actively transcribed from X inactivation center (XIC) and is then deposited in cis on the X chromosome in step-wise manner where associated proteins help to change the chromatin state. The mechanism of contact between Xist and chromatin is still not fully understood. However, the previous reports implicated repetitive region C (repC) in localization of mouse Xist to inactive X chromosome as LNA or PNA oligonucleotides antisense to this region caused Xist detachment from the chromatin. Therefore, a dual toehold LNA CO against repC of mouse Xist was designed and thCHART was performed on crosslinked MEF extract. Sequencing results revealed signal accumulation on chromosome X, with a single dominant peak corresponding to XIC locus (FIG. 6A). The vast majority of signal on chromosome X was found in broad regions spanning almost entirely the length of the whole chromosome and the intensity profile of the broad regions recapitulates the one previously described by CHART. However, Xist thCHART signal on autosomes is dramatically reduced compared to CHART, which is also supported by the decrease in autosomal reads count as well as overall chromosome X signal enrichment (FIG. 6B and FIG. 6C). These results clearly demonstrate that thCHART can be successfully used for RNAs of various lengths that associate with chromatin. Further, thCHART is also easily extendable and adaptable to various CO sequence designs.

thCHART Reveals MSL Complex Spreading on Chromatin

Figure 7A:
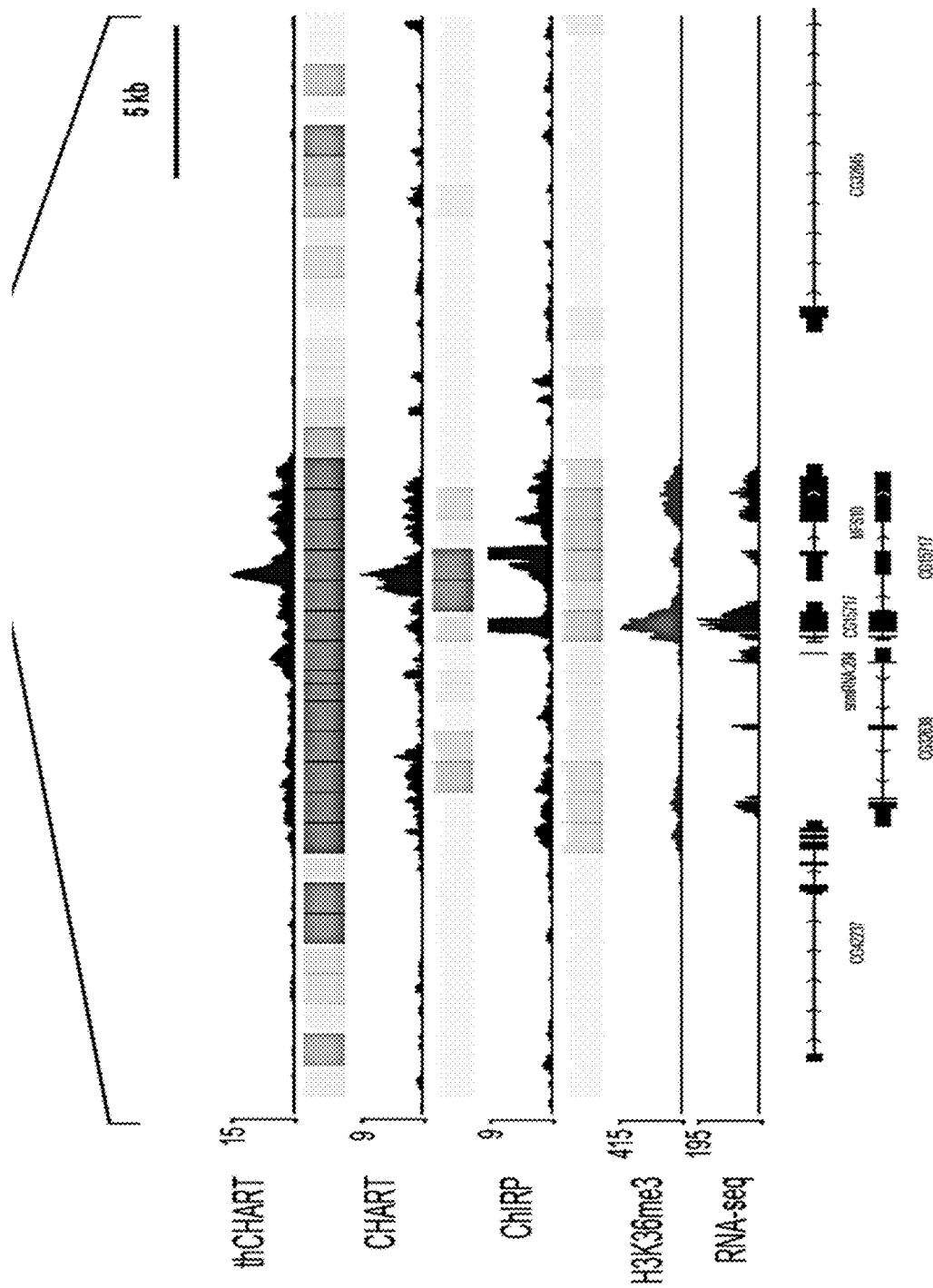
Figure 7C:
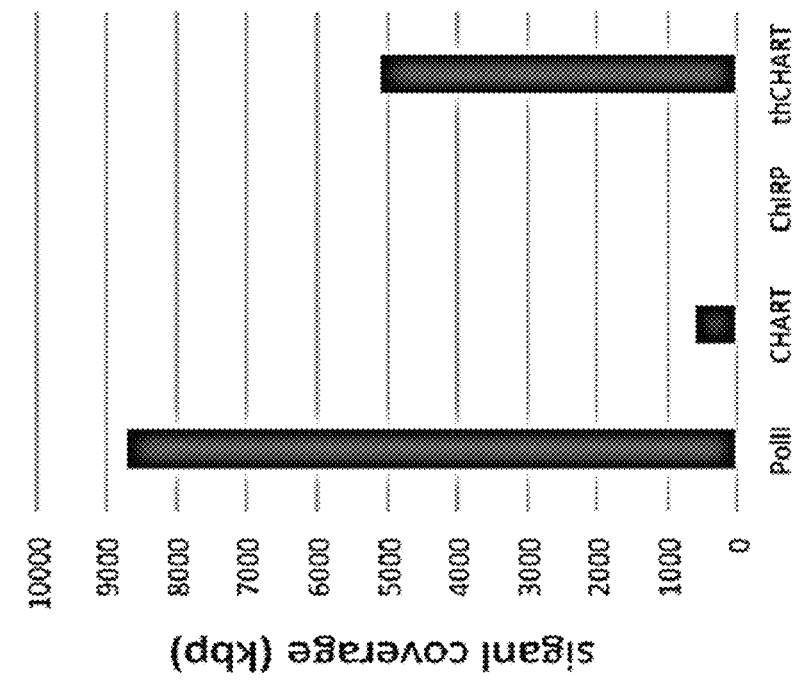
Figure 7B:
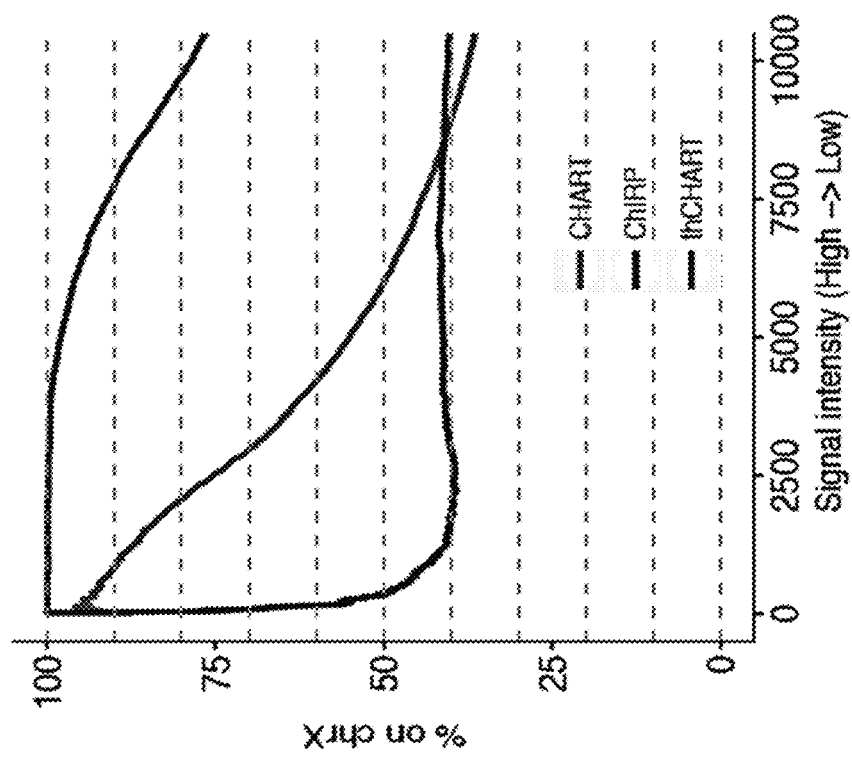

The MSL complex deposition on chromatin happens in multiple steps. First, the assembled complexes accumulate at chromatin entry sites (CES), which contain conserved sequence directly recognized by the MSL2 protein. In the next step, the MSL complex spreads to more distal chromatin regions that contain active genes through MSL3 interacting with H3K36me3 chromatin mark. While interaction at CES are easier to detect due to direct contact of MSL complex with the DNA, the indirect contacts at the distal regions are more challenging to identify. Therefore, experiments were designed to investigate how improvement of signal-to-noise ratio and removal of the background from thCHART data influence distinguishing between true and false positive MSL localization signal at the distal sites. When analyzing biological data, the easiest to detect is the signal with the highest intensity, because of the wide separation between the true signal and the noise introduced by background. However, for parts of data with low intensity, this gap narrows, making it challenging to distinguish the true positives. In order to find out how the signal-background gap changes with decreasing intensity of the signal, fly genomic regions were ordered by roX2 signal intensity from highest to lowest and a cumulative mean of its localization to chromosome X versus autosomes was calculated. While the cumulative mean curves of CHART and ChIRP drop off from 100% level within first two hundred bins indicating contamination of CHART and ChIRP data with high-intensity autosomal signal (FIG. 7B). However, the thCHART curve stays in proximity of 100% mark for more than 3000 bins. To estimate the confidence in data, the ordered bins were split into 10 groups based on the maximal allowed level of autosomal background contamination. The most significant group (90-100%) after correction for background contamination on chromosome X thus represents FDR p-value of 0.112.

Overlaying roX2 data with significance information reveled that CHART, ChIRP and thCHART are sufficiently good in detecting MSL complex peaks found at well-defined chromatin entry sites (FIG. 7A) confirming thus the results from the previous studies. Surprisingly, thCHART data called significant many areas outside of chromatin entry sites. Closer examination revealed that these regions carry hallmarks of active genes such as high levels of H3K36me3 chromatin mark or active transcription as determined by RNA-seq (FIG. 7A, bottom panel). This suggests thCHART can detect genomic regions associated with low intensity MSL complex signal that would otherwise remain undetected by other methods. To determine if thCHART data can identify distal MSL complex sites at active genes genome wide, a meta-analysis of PolII and H3K36me3 ChIP-seq, and RNA-seq mod-ENCODE data from S2 cells was performed. At the highest confidence level (FDR p-value of 0.012) the thCHART detects 200-fold more MSL signal overlapping with active chromosome X regions than ChIRP and 7-fold more that CHART (FIG. 7C through FIG. 7E). This demonstrates how enhanced data quality produced by thCHART improves knowledge about lncRNA and chromatin modifying complexes localization.

thCHART Detects Changes in MSL Complex Spreading Upon Rapid Stress Conditions

The initiation of dosage compensation happens early in drosophila development by localizing MSL complex to the active genes on male chromosome X. The MSL localization pattern is cell type specific and varies between different types of cells depending on the gene expression (DamID paper). However, it is currently unknown whether MSL localization can change within given cell type upon change of gene expression. When introduced to stress conditions, cells respond with a rapid change in gene expression, which helps the cell survival. One of the best studied stress responses is the heat-shock response. Subjecting the cells to temperatures higher that their physiological temperature leads to activation of the heat shock factor (HSF) that enters the cell nucleus and acts as transcription factor. Activation of HSF then leads to activation of several heat-shock related genes, while the bulk of house-keeping genes are down-regulated.

Figure 8A:
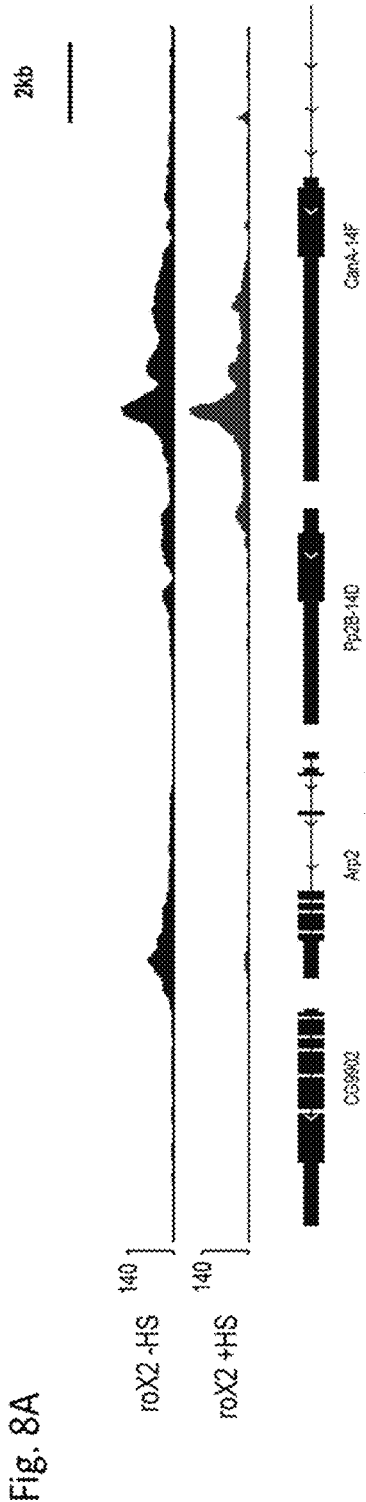
FIG. 8A through FIG. 8C depict exemplary experimental results demonstrating that thCHART can be used to evaluate the effects of cellular conditions on RNA dynamics.

To investigate whether MSL complex localization changes during heat-shock, Drosophila S2 cells were incubated at 37° C. for 1 hour and the MSL complex localization was determined using thCHART against roX2 lncRNA. Comparison of roX2 signal intensity between heat-shock treated and untreated cells revealed substantial number of chromosome X loci with reduced intensity upon heat-shock FIG. 8A. Closer examination of the roX2 signal profiles revealed that high-intensity signal peaks over CES regions were mostly unaffected by the heat-shock treatment. However, many of the distal low intensity signals were found to be significantly reduced or completely diminished in the heat-shock treated cells FIG. 8B.

Figure 8C:
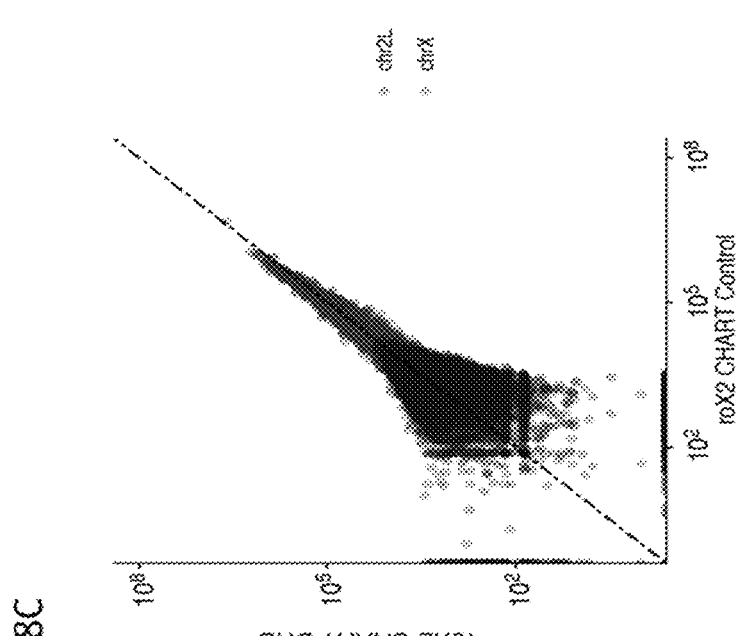
Figure 8B:
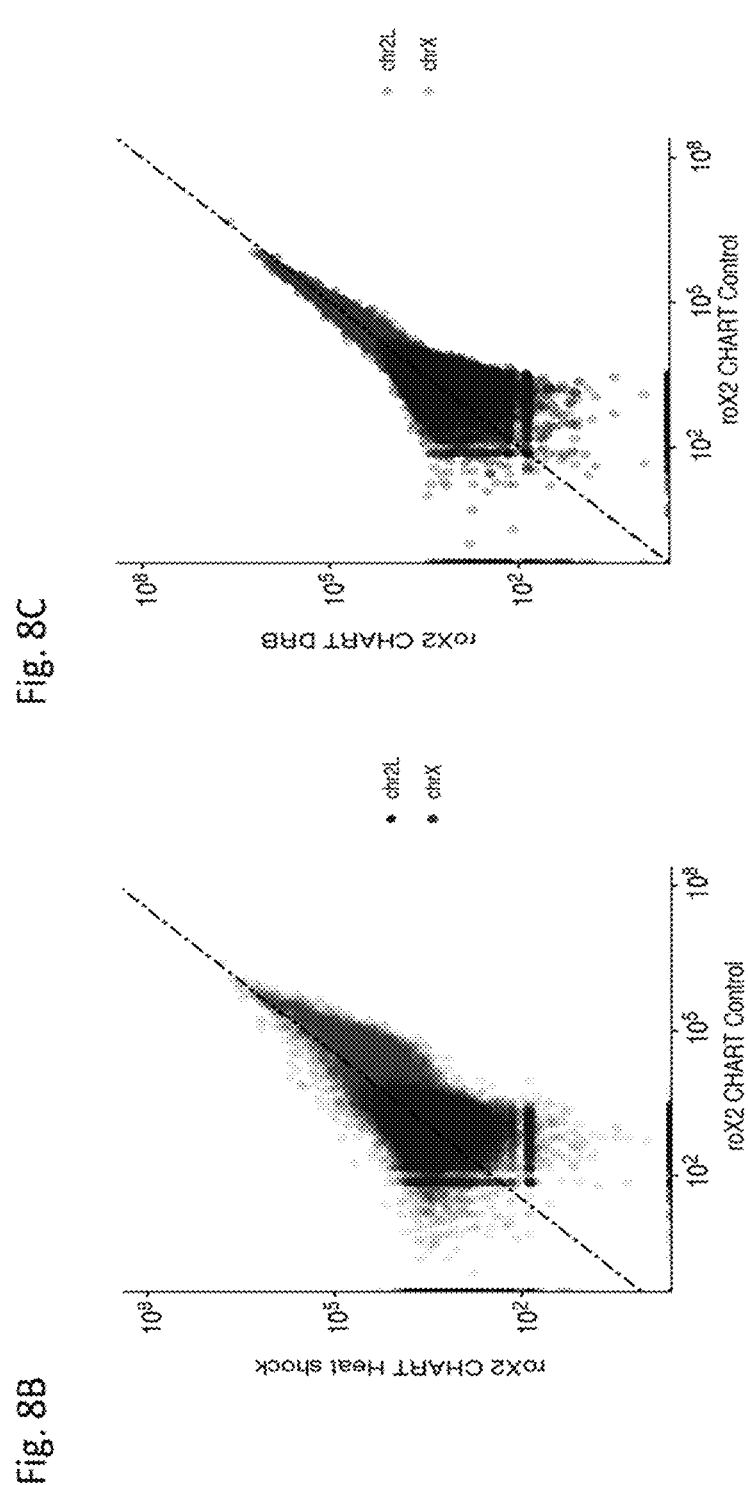

Activation of heat-shock response was previously linked to transcriptional shut down of several house-keeping genes. Without being bound by theory, it was hypothesized that a simple change in gene transcriptional state during heat-shock could be responsible for the observed loss of MSL complex from the distal regions. To test the effect of transcription on MSL complex localization, either 1) transcription was blocked by treating the S2 cells with PolII inhibitor DRB for 3 hours, or 2) gene expression was activated by subjecting the cells to insect hormone 20-Hydroxyecdysone for 24 hours. Surprisingly, comparing the treated cells to their respective control yield no observable changes of MSL complex distribution on the chromosome X (FIG. 8C). This suggests that a simple change in the transcription state of the underlying genes in not sufficient for change of the MSL complex spreading. These results therefore point to the possibility that heat-shock response includes an active mechanism that rapidly change and regulate distribution of chromatin modifying complexes (e.g. MSL complex) on the chromatin.

Example 2

Elucidating the Line-1 RNA-Chromatin Interaction Using Toehold-Chart

In recent years, there has been an increased interest in studying various types of RNA, particularly long non-coding RNAs (lncRNAs). Specific lncRNAs (e.g. Xist, roX2) have been shown to spread across the chromatin of the entire chromosome and regulate gene expression by changing the state of the surrounding chromatin (Simon et al., 2013, Nature, 504:465-469; Simon et al., 2011, Proc Natl Acad Sci USA, 108:20497-20502). Long interspersed elements (LINEs) form up to 18% of our genetic information, but yet have received very little attention. These elements typically contain their own internal PolII promoter, which drives transcription of the 6 kb long LINE-1 RNA transcript coding for two polypeptides necessary for the element transposition (Padeken et al., 2015, Curr. Opin. Genet. Dev. 31:12-19; Finnegan, 2012, Curr Biol 22, R432-437). Except for a few cases where LINE-1 element influences expression of the neighboring genes, these elements have generally been considered as junk DNA without function (Palazzo and Gregory, 2014, PLoS Genet, 10:e1004351). Interestingly, recent studies suggest that LINE-1 RNAs can stably associate with chromatin (Donley et al., 2013, PLoS Genet, 9:e1003423; Hall et al., Cell, 156:907-919; Donley et al., 2015, PLoS Genet, 11:e1004923). Sequencing RNA from cells where transcription was inhibited revealed that 34% of the chromatin-associated RNA signal comes from repetitive elements (Mondal et al., 2010, Genome Res. 20:899-907). FISH studies have shown that LINE-1 RNA spreads along chromosomes and stays tightly associated with the chromatin even after transcription block (Hall et al., Cell, 156:907-919). This behavior seems to be species specific, as human LINE-1 RNA does not spread on a mouse chromosome or vice versa, when a single human chromosome is introduced into mouse cells (Hall et al., Cell, 156:907-919). The function of LINE-1 RNA on chromatin is not known, but disrupting recently discovered LINE-1 element called ASAR6 led to severe case of delayed replication timing and mitotic condensation. This therefore brings and intriguing possibility that chromatin associated LINE-1 RNA might regulate chromatin state and replication timing in similar way as Xist ncRNA does on the X chromosome (Donley et al., 2013, PLoS Genet, 9:e1003423; Thayer, 2012, Bioessays, 34:760-770; Diaz-Perez et al., 2006, Genetics, 174: 1115-1133). How LINE-1 RNA spreads on the chromatin? Does this spreading occur in cis or trans? What ensures and maintains the specificity of this interaction? To answer these questions, I will create stable cell lines expressing a single tagged ASAR6 LINE-1 element and apply Capture hybridization analysis of RNA targets (CHART) method to identify its spreading pattern and proteins responsible for chromatin association. CHART (FIG. 1A) and other oligonucleotide hybridization based methods were successfully used to study highly expressed RNAs such as Xist and Malat-1.1 (West et al., 2014, Mol Cell, 55:791-802). However, all these approaches are particularly challenging to apply to similar repetitive elements, because of the potential for undesired high background signals, which makes these methods unsuitable for studying low expressed RNAs such as LINE-1 RNA. To alleviate these limitations, a novel method called toehold CHART (thCHART) has been developed that utilizes locked nucleic acid (LNA) (Braasch and Corey, 2001, Chem. Biol, 8:1-7; Wahlestedt et al., 2000, Proc Natl Acad Sci USA, 97:5633-5638; You et al., 2006, Nucleic Acids Res, 34:e60) nucleotides to increase affinity and toehold technology to improve specificity towards target RNA (Wu et al., 2015, Nat Methods; 12:1191-1196; Zhang et al., 2012, Nat Chem, 4:208-214).

Develop thCHART Method to Investigate LINE-1 Interaction with Chromatin

Figure 9A:
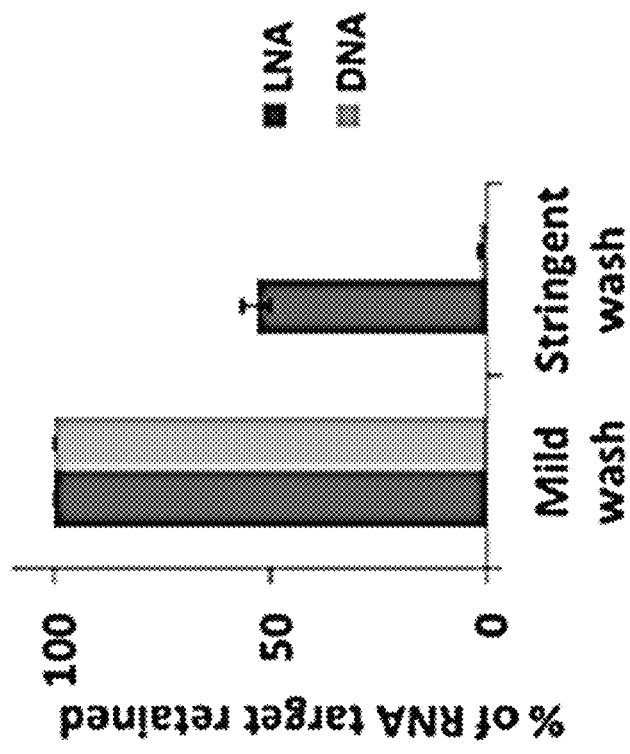
FIG. 9A through FIG. 9B depict exemplary experimental results demonstrating that LNA improves affinity of capture oligonucleotide.
Figure 9B:
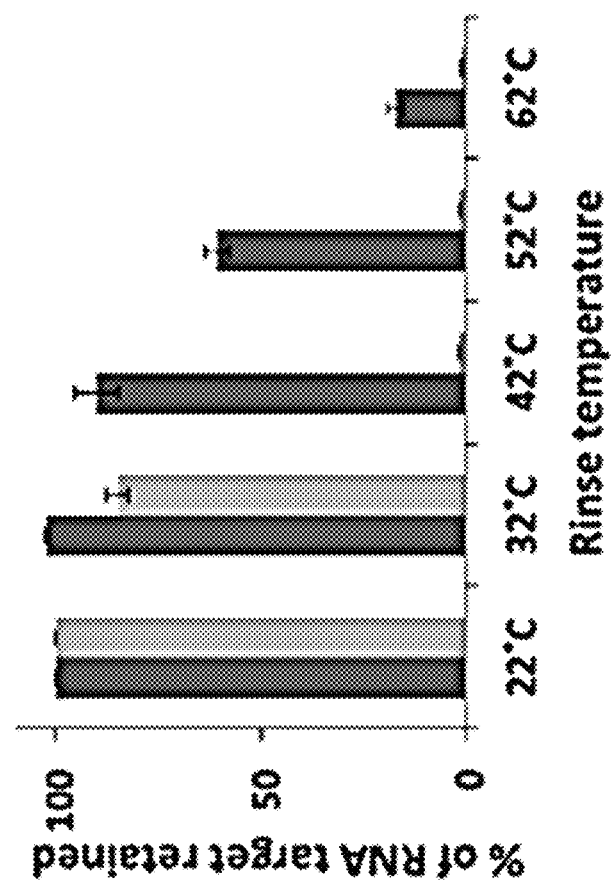
Figure 10:
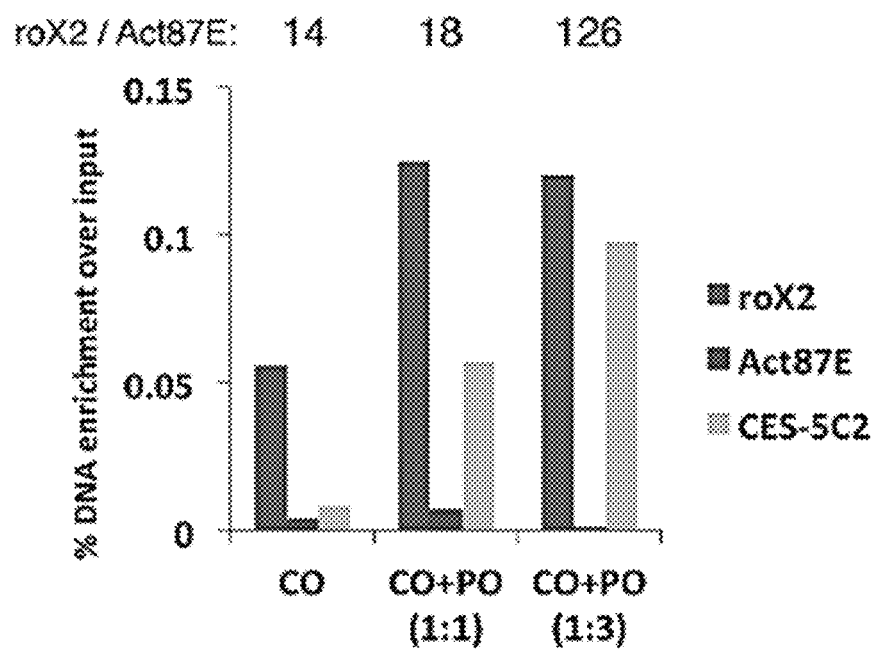
FIG. 10 depicts exemplary experimental results demonstrating that LNA toehold CO improves signal-to-background ration of CHART Capture-protector oligonucleotide hybrids against roX2 RNA were used at indicated ratio to perform CHART on formaldehyde cross-linked S2 cell extract. Eluted DNA was assayed using qPCR. RoX2 and CES-5C2 genes are known roX2 RNA binding sites. Act87E gene serves as off-target.

To improve specificity of CHART, LNA nucleotides are used in capture oligonucleotide sequence, which greatly increases binding affinity to target RNA (Braasch and Corey, 2001, Chem. Biol, 8:1-7). This allows for more stringent washing conditions to be used to remove unwanted background, while preserving the desired signal. However, the LNA oligonucleotide annealing reaction has a very negative standard free energy ($\Delta G \ll 0$) at room temperature, which would cause spurious binding to off-target nucleic acids. To circumvent this problem, toehold technology is used (Wu et al., 2015, Nat Methods; 12:1191-1196; Zhang et al., 2012, Nat Chem, 4:208-214). This system uses an additional complementary protecting oligonucleotide (PO), which is pre-hybridized to the capture oligonucleotide (FIG. 1A). The capture oligonucleotide therefore consists of three regions: 1) a short single-stranded region complementary only to the target called "toehold", 2) a central region complementary to both target and protecting oligonucleotide and 3) a second "protecting toehold" complementary only to the protector. The hybridization starts with toehold annealing to the target, followed by strand exchange through branch migration and is finishes by releasing the protector. The presence of the "protecting toehold" causes the protector to behave as a target competitor, which allows the reverse reaction to proceed with the same fast kinetics. Therefore, by rational designing of the sequences of both toeholds $\Delta G \approx 0$ can be achieved, which allows the hybridization specificity to be easily fine-tuned by simply changing the total protector concentration in the reaction (Wu et al., 2015, Nat Methods; 12:1191-1196; Wang and Zhang, 2015, Nat Chem 7, 545-553). Experimental data confirms that incorporating LNA bases into a capture oligonucleotide leads to dramatic increase in the affinity to target RNA. The LNA capture oligonucleotide is capable of retaining 90% of the RNA target after washing the hybrids with 35% Formamide at 42° C. (FIG. 9A). Furthermore, combining these rinses with washes under denaturing conditions showed that the LNA oligonucleotide still retained 34 times more target RNA than a conventional DNA oligonucleotide (FIG. 9B). In agreement with predictions, the LNA capture oligonucleotide is also capable of undergoing toehold-mediated strand exchange with target RNA at various concentrations (FIG. 1D). Using the LNA toehold capture oligonucleotide in a CHART experiment on roX2 ncRNA demonstrates increased DNA recovery of two roX2 high-affinity binding sites. In addition, increasing the concentration of the protector improves the signal-to-background ratio from 18 to 126 (FIG. 10). These results demonstrate that LNA toehold technology can be successfully used to study RNA biochemistry, including to study LINE-1 RNA.

Establish Cell Line(s) with an Integrated Single Tagged ASAR6 LINE-1 Element

Figure 11:
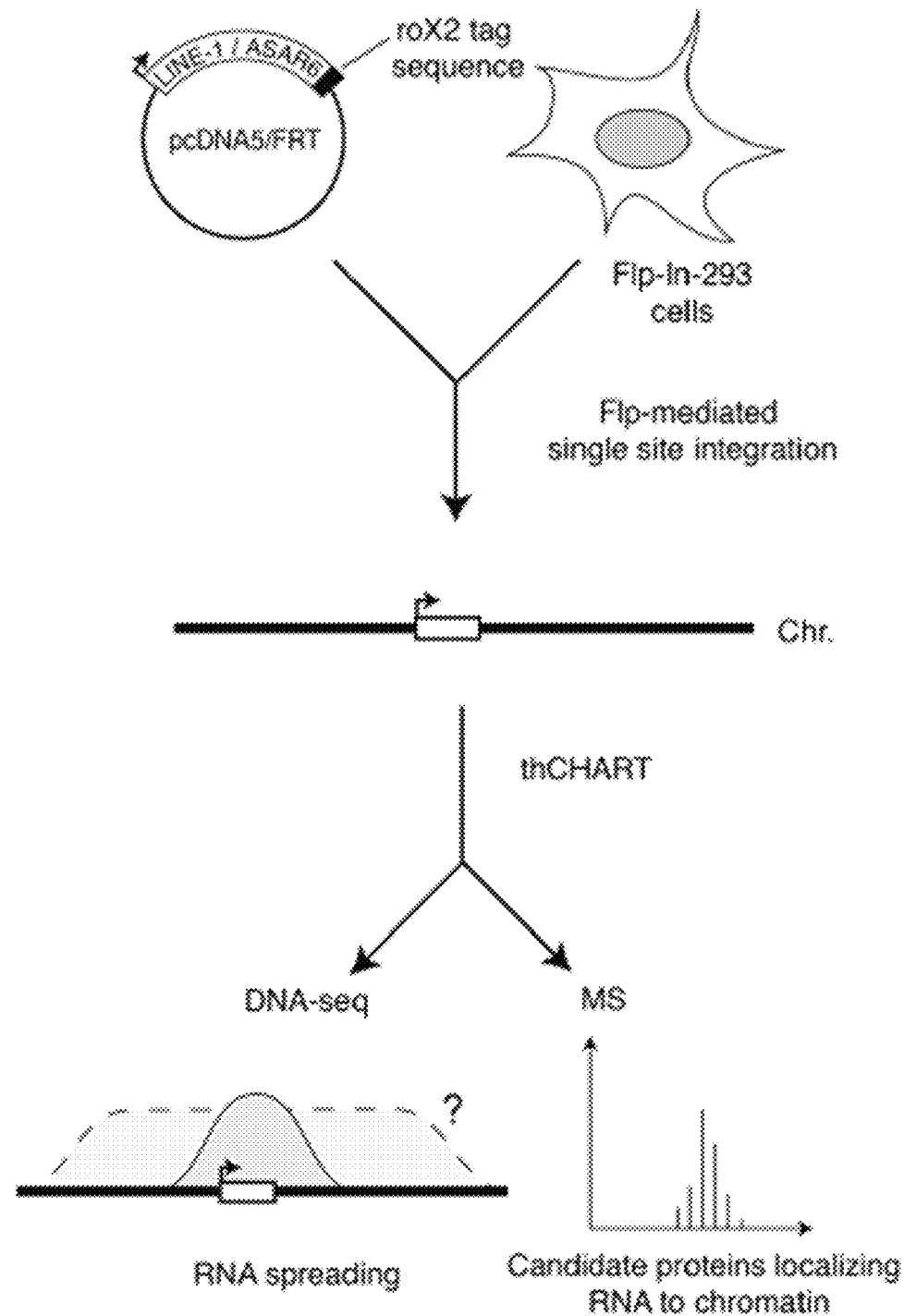
FIG. 11 depicts a schematic diagram of the ASAR6 LINE-1 element study. ASAR6 LINE-1 sequence tagged with roX2-tag will be cloned into pcDNA5/FRT plasmid and transfected into Flp-In-293 cells to create stable integration at defined genomic locus. Cells with integrated transgene will be used for thCHART to identify sites of chromatin contact and interacting proteins.

It is not clear whether LINE-1 RNA spreading occurs only in cis or also in trans, and whether a single LINE-1 element is sufficient to cover the whole chromosome with its RNA. To answer these questions, experiments are designed to study the behavior of a single LINE-1 element integrated in a defined genomic position. The full length ASAR6 LINE-1 sequence is cloned into the pcDNA5/FRT plasmid available from Thermo Fisher Scientific (FIG. 11). Since LINE-1 elements contain their own internal PolII promoter, the default CMV promoter is disabled using the Phusion site-directed mutagenesis kit (Thermo Fisher Scientific). To ensure distinguishability from endogenously expressed LINE-1 elements a 25 nt sequence from Drosophila roX2 ncRNA is inserted into the LINE-1 3'UTR as a tag. This sequence is 1) unique to roX2, 2) is not present in the human transcriptome and 3) was proved to be useful for performing thCHART in preliminary experiments (FIG. 11). The pcDNA5/FRT plasmid is co-transfected with the pOG44 plasmid coding for Flp recombinase into human Flp-In 239T cells (Fisher Scientific), which contain a single FRT site where the pcDNA5/FRT plasmid is integrated. Cells are selected using Hygromycin and successful integration is validated with PCR of genomic DNA using primers specific for the transgene and FRT locus. Further, efficient transcription of the tagged LINE-1 gene is determined using FISH or RT-qPCR against roX2 tag sequence. This results in the generation of a cell system to systematically test the molecular underpinnings of LINE-1 RNA mediated interaction with chromatin.

Determine ASAR6 LINE-1 Element RNA Spreading and Interaction with Chromatin

To determine whether LINE-1 RNA associates with chromatin in cis or trans, and how far the RNA spreads from its gene of origin, the established cell line is used to perform thCHART on roX2-tagged ASAR6 LINE-1 RNA. The ratio of anti-roX2 capture and the protecting oligonucleotide pair (FIG. 11) will be determined to achieve maximal hybridization yield and minimal offtarget binding. Purified complexes will be washed using stringent conditions (FIG. 9B), decrosslinked and eluted using proteinase K treatment. thCHART in parental Flp-In cells and/or using antisense capture oligonucleotide is used as a negative control. Recovered DNA is sequenced using high throughput sequencing. Data is analyzed using the previously described pipeline (Simon et al., 2013, Nature, 504:465-469) with modifications to preserve repetitive sequences. The mechanism of chromatin attachment of many RNAs including LINE-1 RNA is still unknown (Hall et al., Cell, 156:907-919). Previous reports suggest that hnRNP U/SAF-A could a play role in this process as expression of a dominant negative mutant of hnRNP U released LINE-1 RNA to the nucleoplasm (Hall et al., Cell, 156:907-919). To uncover proteins involved in retaining LINE-1 RNA on chromatin, ASAR6 LINE-1 cells are used to perform thCHART coupled with mass spectrometry (thCHART MS). The experiment is performed as described above with eluting the co-purified proteins using RNAse treatment. Recovered proteins are analyzed by tandem mass spec trometry. Fragment intensities are compared with negative controls to eliminate false positive hits. To validate the roles of significantly enriched candidates in RNA-chromatin interactions, protein expression is knocked down using siRNA transfection or knocked-out using the Cas9 system. The effect on RNA-chromatin interaction is determined with thCHART coupled with qPCR or by FISH using probes against the LINE-1 sequence. Validated proteins are further investigated for their role in delayed replication timing. These experiments provide insight into the role of chromatin-associated repetitive element RNA and help to better understand how cells regulate DNA replication timing.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for identifying a binding partner of a nucleic acid molecule of interest, the method comprising the steps of:
   a) contacting a complex comprising a target nucleic acid molecule with nucleic acid molecule comprising a duplex formed from hybridization of at least one protector oligonucleotide (PO) with at least one capture oligonucleotide (CO),
   wherein the CO comprises a 5' toehold region, a central region, wherein the central region comprises a nucleotide sequence that is complementary to a nucleotide sequence of a target nucleic acid molecule and further comprises at least one modification, and a 3' toehold region, and further wherein the 5' toehold region of the CO comprises a nucleotide sequence that is complementary to a nucleotide sequence of the target nucleic acid molecule and wherein the 3' toehold region of the CO comprises a nucleotide sequence that is complementary to a nucleotide sequence of the PO but not to the target nucleic acid molecule; and
   wherein the PO comprises a nucleotide sequence complementary to the central region and one of the 5' toehold region and the 3' toehold region of the CO, such that strand exchange occurs between the CO and the complex comprising a target nucleic acid molecule to form a CO:target complex;
   b) washing the CO:target complex;
   c) immunoprecipitating the CO:target complex; and
   d) eluting at least one component of the complex comprising the target nucleic acid molecule.

2. The method of claim 1, wherein the 3' toehold region CO comprises a nucleotide sequence that is complementary to a nucleotide sequence of a target nucleic acid molecule and wherein the 5' toehold region of the CO comprises a nucleotide sequence that is complementary to a nucleotide sequence of a PO.

3. The method of claim 1, wherein the CO further comprises a tag for affinity purification.

4. The method of claim 1, wherein the CO comprises at least one locked nucleic acid (LNA) modification in the central region.

5. The method of claim 4, wherein the PO is an RNA oligonucleotide.

6. The method of claim 5, wherein the CO:PO complex comprises a RNA:DNA hybrid molecule comprising a ssDNA overhang which serves as one of a 5' toehold region and a 3' toehold region.

7. The method of claim 6, wherein the ssDNA overhang comprises at least 4 nucleotides.

8. The method of claim 1, wherein step d) comprises contacting the CO:target complex with an elution oligonucleotide (EO), wherein the EO comprises a nucleotide sequence complementary to the full length of the CO.

9. The method of claim 1, wherein the target nucleic acid molecule is crosslinked to at least one of a nucleic acid molecule and a protein, and wherein step d) further comprises a step of reversing the crosslinks.

10. The method of claim 1, wherein the target nucleic acid molecule is in a complex with at least one nucleic acid molecule wherein the method further comprises the steps of:
- e) ligating at least one adaptor molecule to an eluted nucleic acid molecule,
- f) amplifying the eluted nucleic acid molecule, and
- g) sequencing the amplified products.

* * * * *